US012099046B2

(12) United States Patent
Brooks et al.

(10) Patent No.: US 12,099,046 B2
(45) Date of Patent: Sep. 24, 2024

(54) MANUFACTURING A BIOLOGIC PHARMACEUTICAL USING CAUSAL MODELS

(71) Applicant: Solventum Intellectual Properties Company, Maplewood, MN (US)

(72) Inventors: Brian E. Brooks, St. Paul, MN (US); Gilles J. Benoit, Minneapolis, MN (US); Peter O. Olson, Andover, MN (US); Tyler W. Olson, Woodbury, MN (US); Himanshu Nayar, St. Paul, MN (US); Frederick J. Arsenault, Stillwater, MN (US); Nicholas A. Johnson, Woodbury, MN (US); Susan L Woulfe, Woodbury, MN (US); Mark A. Tomai, Hudson, WI (US)

(73) Assignee: Solventum Intellectual Properties Company, Maplewood, MN (US)

( * ) Notice: Subject to any disclaimer, the term of this patent is extended or adjusted under 35 U.S.C. 154(b) by 334 days.

(21) Appl. No.: 17/436,770

(22) PCT Filed: Oct. 3, 2019

(86) PCT No.: PCT/IB2019/058426
§ 371 (c)(1),
(2) Date: Sep. 7, 2021

(87) PCT Pub. No.: WO2020/188335
PCT Pub. Date: Sep. 24, 2020

(65) Prior Publication Data
US 2022/0178899 A1 Jun. 9, 2022

Related U.S. Application Data

(60) Provisional application No. 62/818,816, filed on Mar. 15, 2019, provisional application No. 62/898,834, filed on Sep. 11, 2019.

(51) Int. Cl.
*G05B 13/04* (2006.01)
*B01J 19/00* (2006.01)
*G01N 33/15* (2006.01)

(52) U.S. Cl.
CPC .......... *G01N 33/15* (2013.01); *B01J 19/0013* (2013.01); *B01J 19/0033* (2013.01); *G05B 13/041* (2013.01)

(58) Field of Classification Search
CPC ... G01N 33/15; B01J 19/0013; B01J 19/0033; G05B 13/041
See application file for complete search history.

(56) References Cited

U.S. PATENT DOCUMENTS 5,196,997 A 3/1993 Kurtzberg
5,882,774 A 3/1999 Jonza
(Continued)

FOREIGN PATENT DOCUMENTS

CA 2977272 2/2018
CN 101419216 A 4/2009
(Continued)

OTHER PUBLICATIONS

European Patent Office Supplementary European Search Report for EP Application No. 19920541, 7 pages, Dec. 12, 2022.
(Continued)

*Primary Examiner* — Gary Collins

(57) ABSTRACT

Methods, systems, and apparatus, including computer programs encoded on a computer storage medium, for optimizing a process of manufacturing a biologic pharmaceutical. In one aspect, the method comprises repeatedly performing the following: i) selecting a configuration of input settings for manufacturing a batch of a biologic pharmaceutical based on a causal model that measures current causal relationships between input settings and a measure of a quality of batches (Continued)

of the biological pharmaceutical; ii) determining a measure of the quality of a batch of the biological pharmaceutical manufactured using the configuration of input settings; and iii) adjusting, based on the measure of the quality of the batch of the biological pharmaceutical, the causal model.

17 Claims, 20 Drawing Sheets

(56) References Cited

U.S. PATENT DOCUMENTS

| | | | |
|---|---|---|---|
| 5,976,424 | A | 11/1999 | Weber |
| 6,151,582 | A | 11/2000 | Huang |
| 6,266,853 | B1 | 7/2001 | Ho |
| 6,594,024 | B1 | 7/2003 | Singh |
| 6,952,688 | B1 | 10/2005 | Goldman |
| 7,461,040 | B1 | 12/2008 | Goldman |
| 7,680,752 | B1 | 3/2010 | Clune, III |
| 9,541,471 | B2 * | 1/2017 | McCready ......... G05B 23/0254 |
| 9,679,258 | B2 | 6/2017 | Mnih |
| 9,947,018 | B2 | 4/2018 | Brooks |
| 10,133,983 | B1 | 11/2018 | Chelian |
| 10,190,792 | B2 | 1/2019 | Jacobson |
| 10,229,026 | B1 | 3/2019 | Vijendra |
| 10,628,733 | B2 | 4/2020 | Schaul |
| 11,113,605 | B2 | 9/2021 | Czarnecki |
| 2001/0047846 | A1 | 12/2001 | Currens |
| 2003/0051737 | A1 | 3/2003 | Hickle |
| 2004/0099993 | A1 | 5/2004 | Jackson |
| 2004/0230397 | A1 | 11/2004 | Chadwick |
| 2005/0096637 | A1 | 5/2005 | Heruth |
| 2006/0047538 | A1 | 3/2006 | Condurso |
| 2006/0167579 | A1 | 7/2006 | Fujii |
| 2006/0242288 | A1 | 10/2006 | Masurkar |
| 2006/0274244 | A1 | 12/2006 | Battiato |
| 2007/0031853 | A1 | 2/2007 | Stanton |
| 2007/0156294 | A1 | 7/2007 | Tipping |
| 2007/0156382 | A1 | 7/2007 | Graham, II |
| 2007/0208322 | A1 | 9/2007 | Rantala |
| 2007/0219736 | A1 | 9/2007 | Okita |
| 2008/0013821 | A1 | 1/2008 | Macgregor et al. |
| 2008/0121729 | A1 | 5/2008 | Gray |
| 2008/0306770 | A1 | 12/2008 | Sysko et al. |
| 2009/0006125 | A1 | 1/2009 | Angell |
| 2009/0204267 | A1 | 8/2009 | Sustaeta |
| 2010/0103521 | A1 | 4/2010 | Smith |
| 2010/0191361 | A1 | 7/2010 | McCready |
| 2010/0201242 | A1 | 8/2010 | Liu |
| 2010/0330155 | A1 | 12/2010 | Berry |
| 2011/0022193 | A1 | 1/2011 | Panaitescu |
| 2011/0112997 | A1 | 5/2011 | Sabe |
| 2011/0132370 | A1 | 6/2011 | Farrugia |
| 2011/0276164 | A1 * | 11/2011 | Bourg, Jr. ............ G05B 13/042 700/104 |
| 2012/0010867 | A1 | 1/2012 | Eder |
| 2013/0038939 | A1 | 2/2013 | Walker, Jr. |
| 2013/0132108 | A1 | 5/2013 | Solilov |
| 2013/0197675 | A1 | 8/2013 | McCarthy |
| 2013/0197698 | A1 | 8/2013 | Shah |
| 2014/0025358 | A1 | 1/2014 | Hill |
| 2014/0136146 | A1 * | 5/2014 | McCready ......... G05B 23/0254 702/179 |
| 2014/0289174 | A1 | 9/2014 | Statnikov |
| 2014/0379101 | A1 | 12/2014 | Buchmann |
| 2015/0142704 | A1 | 5/2015 | London |
| 2016/0041541 | A1 | 2/2016 | Drees |
| 2016/0147203 | A1 | 5/2016 | Di Cairano |
| 2016/0274570 | A1 | 9/2016 | Shih et al. |
| 2016/0287693 | A1 | 10/2016 | Norman |
| 2016/0350796 | A1 | 12/2016 | Arsenault |
| 2017/0031354 | A1 | 2/2017 | Tyber |
| 2017/0050590 | A1 | 2/2017 | List |
| 2017/0102678 | A1 | 4/2017 | Nixon |
| 2017/0109642 | A1 | 4/2017 | Kawale |
| 2017/0278114 | A1 | 9/2017 | Renders |
| 2017/0359418 | A1 | 12/2017 | Sustaeta |
| 2018/0121817 | A1 | 5/2018 | Datta |
| 2018/0181808 | A1 | 6/2018 | Sridharan |
| 2018/0242429 | A1 | 8/2018 | Ashdown |
| 2018/0364657 | A1 | 12/2018 | Luo |
| 2019/0026754 | A1 | 1/2019 | Miltonberger |
| 2019/0078801 | A1 | 3/2019 | Turney |
| 2019/0175810 | A1 | 6/2019 | Quiroz |
| 2019/0244110 | A1 | 8/2019 | Qiu |
| 2019/0326002 | A1 | 10/2019 | Mould |
| 2022/0257181 | A1 | 8/2022 | Wang |

FOREIGN PATENT DOCUMENTS

| | | |
|---|---|---|
| CN | 108710289 | 10/2018 |
| EP | 3316140 | 5/2018 |
| JP | 2006-277370 | 10/2006 |
| JP | 2013080458 A | 5/2013 |
| WO | WO 2005-124580 | 12/2005 |
| WO | WO 2012-151499 | 11/2012 |
| WO | WO 2013-130956 | 9/2013 |
| WO | 2016051398 A1 | 4/2016 |
| WO | WO 2016-086665 | 6/2016 |
| WO | WO 2020-109937 | 6/2020 |
| WO | WO 2020-188327 | 9/2020 |
| WO | WO 2020-188328 | 9/2020 |
| WO | WO 2020-188329 | 9/2020 |
| WO | WO 2020-188330 | 9/2020 |
| WO | WO 2020-188331 | 9/2020 |
| WO | WO 2020-188333 | 9/2020 |
| WO | WO 2020-188334 | 9/2020 |
| WO | WO 2020-188336 | 9/2020 |
| WO | WO 2020-188338 | 9/2020 |
| WO | WO 2020-188341 | 9/2020 |
| WO | WO 2020-190324 | 9/2020 |
| WO | WO 2020-190325 | 9/2020 |
| WO | WO 2020-190326 | 9/2020 |
| WO | WO 2020-190327 | 9/2020 |
| WO | WO 2020-190328 | 9/2020 |

OTHER PUBLICATIONS

Alvarez, "Introduction to Adaptive Experimental Design", Center for Quantitative Sciences, Vanberbilt University School of Medicine, Oct. 12, 2012, 96 pages.
Agrawal, "Analysis of Thompson Sampling for the Multi-armed Bandit Problem", Conference on Learning Theory, 2012, vol. 23, pp. 39.1-39.26.
Auer, "Finite-time Analysis of the Multiarmed Bandit Problem", Machine Learning, 2002, vol. 47, pp. 235-256.
Cao, "Nearly Optimal Adaptive Procedure with Change Detection for Piecewise-Stationary Bandit", International Conference on Artificial Intelligence and Statistics, 2019, vol. 89, 10 pages.
Cesa-Bianchi, "Boltzmann Exploration Done Right", Conference on Neural Information Processing Systems, 2017, pp. 1-10.
Gomes, "Machine-Learning Maestro Michael Jordon on the Delusions of Big Data and Other Huge Engineering Efforts", IEEE Spectrum, Oct. 2014, 10 pages.
Jordan, "Machine Learning: Trends, Perspectives, and Prospects", Journal of Science, Jul. 17, 2015, vol. 349, No. 6245, pp. 255-260.
Li, "A Contextual-Bandit Approach to Personalized News Article Recommendation", International World Wide Web Conference (WWW), 2010, pp. 661-670.
Li, "Knowledge Discovery from Observational Data for Process Control using Causal Bayesian Networks", IIE Transactions, 2007, vol. 39, pp. 681-690.
Pike-Burke, "Bandits with Delayed, Aggregated Anonymous Feedback", International Conference on Machine Learning, 2018, 9 pages.
Shi, "Quality Control and Improvement for Multistage Systems: A survey", IIE Transactions, 2009, vol. 41, No. 9, pp. 744-753.
International Search Report for PCT International Application No. PCT/IB2019/057646, mailed on Dec. 17, 2019, 4 pages.

(56) References Cited

OTHER PUBLICATIONS

International Search Report for PCT International Application No. PCT/IB2019/058423 mailed on Jan. 17, 2020, 3 pages.
International Search Report for PCT International Application No. PCT/IB2019/058426 mailed on, Jan. 17, 2020, 3 pages.
International Search Report for PCT International Application No. PCT/IB2019/058424 mailed on Jan. 17, 2020, 3 pages.
International Search Report for PCT International Application No. PCT/IB2019/057662 mailed on May 1, 2020, 3 pages.
International Search Report for PCT International Application No. PCT/IB2019/058438 mailed on Apr. 24, 2020, 3 pages.
International Search Report for PCT International Application No. PCT/US2019/050703 mailed on Dec. 4, 2019, 3 pages.
International Search Report for PCT International Application No. PCT/US2019/050695 mailed on Nov. 27, 2019, 3 pages.
International Search Report for PCT International Application No. PCT/IB2019/057648, mailed on Jan. 24, 2020, 7 pages.
International Search Report for PCT International Application No. PCT/IB2019/058428, mailed on Jan. 17, 2020, 3 pages.
International Search Report for PCT International Application No. PCT/IB2019/059227, mailed on Jan. 27, 2020, 3 pages.
International Search Report for PCT International Application No. PCT/IB2019/050701, mailed on Jan. 13, 2020, 5 pages.
International Search Report for PCT International Application No. PCT/IB2019/057664, mailed on May 4, 2020, 3 pages.
International Search Report for PCT International Application No. PCT/US2019/050699, mailed on Dec. 5, 2019, 3 pages.
International Search Report for PCT International Application No. PCT/US2019/050691, mailed on Dec. 11, 2019, 3 pages.
International Search Report for PCT International Application No. PCT/IB2019/057673, mailed on May 12, 2020, 2 pages.
Li, Jing et al., "Knowledge discovery from observational data for process control using causal Bayesian networks," IIE Transactions, vol. 39, pp. 681-690, 2007.

* cited by examiner

MANUFACTURING A BIOLOGIC PHARMACEUTICAL USING CAUSAL MODELS

CROSS REFERENCE TO RELATED APPLICATIONS

This application is a national stage filing under 35 U.S.C. 371 of PCT/IB2019/058426, filed Oct. 3, 2019, which claims the benefit of U.S. Provisional Application Nos. 62/818,816, filed Mar. 15, 2019, and 62/898,834, filed Sep. 11, 2019, the disclosures of which are incorporated by reference in their entireties herein.

BACKGROUND

This specification relates to controlling one or more biologic pharmaceutical sites and to determining causal relationships between control settings for manufacturing a biologic pharmaceutical at the sites and environment responses received from the biologic pharmaceutical sites.

Existing techniques for determining which control settings should be used to control an environment generally employ either modeling-based techniques or rely on active control of the system.

In modeling-based techniques, the system passively observes data, i.e., historical mappings of control settings to environment responses, and attempts to discover patterns in the data to learning a model that can be used to control the environment. Examples of modeling-based techniques include decision forests, logistic regression, support vector machines, neural networks, kernel machines and Bayesian classifiers.

In active control techniques, the system relies on active control of the environment for knowledge generation and application. Examples of active control techniques include randomized controlled experimentation, e.g., bandit experiments.

SUMMARY

This specification describes systems and methods implemented as computer programs on one or more computers in one or more locations that select control settings for manufacturing a biologic pharmaceutical.

According to a first aspect there is provided a method comprising repeatedly performing the following: i) selecting a configuration of input settings for manufacturing a batch of a biologic pharmaceutical based on a causal model that measures current causal relationships between input settings and a measure of a quality of batches of the biological pharmaceutical; ii) determining a measure of the quality of a batch of the biological pharmaceutical manufactured using the configuration of input settings; and iii) adjusting, based on the measure of the quality of the batch of the biological pharmaceutical, the causal model.

In some implementations, the method further comprises selecting the configuration of input settings based on a set of internal control parameters, and adjusting the internal control parameters based on the measure of the quality of the batch.

In some implementations, the measure of the quality of the batch comprises one or more of the following: a yield of the batch; a measure of an activity of the batch; a measure of an efficacy of the batch; a measure of impurities in the batch; a measure of a viability of transfected cells; a measure of transfection efficiency; a measure of a purity of the biologic pharmaceutical; a measure of monodispersion; or a measure of cell density. In some implementations, the purity of the biologic pharmaceutical comprises one or more of the following: a measure of host cell protein impurity; a measure of DNA impurity; a measure of RNA impurity; or a measure of host cell metabolite impurity.

In some implementations, the input settings comprise one or more of the following: one or more settings related to processing steps; one or more settings related to a chemical composition of a substance; one or more settings related to physical control during manufacturing; or one or more settings related to purifying the batch of the biologic pharmaceutical. In some implementations, the settings related to processing steps comprise one or more of the following: an ordering of the processing steps; a time spent in each processing step; a time spent in each subprocess of a given processing step; or a choice of parameters for each processing step. In some implementations, the settings related to a chemical composition comprise a selection of one or more of a nutrient media; an ion exchange resin; an affinity chromatography matrix; a polymer; a wash buffer; or an elution buffer. In some implementations, the settings related to physical control during manufacturing comprise one or more of a time of manufacturing; a time of purification; a temperature during manufacturing; a temperature during purification; a humidity during manufacturing; a humidity during purification; a flow rate used during manufacturing; a flow rate used during purification; a g-force used during manufacturing; a measure of magnetism used during manufacturing; a measure of electricity used during manufacturing; or a measure of agitation used during manufacturing. In some implementations, the settings related to purifying the batch of the biologic pharmaceutical comprise purifying the batch using one or more of: electrostatic interactions; hydrophobic interactions; hydrophilic interactions; affinity chromatography; or size exclusion chromatography.

In some implementations, the method further comprises selecting the configuration based on the causal model and a predetermined set of external variables, and the method further comprises adjusting control parameters that parameterize the impact of the predetermined set of external variables. In some implementations, the predetermined set of external variables comprises one or more external variables related to an environmental climate during manufacturing. In some such implementations, the external variables related to the environmental climate comprise one or more of the following: a humidity during manufacturing; an external temperature during manufacturing; or a level of light during manufacturing.

Particular embodiments of the subject matter described in this specification can be implemented so as to realize one or more of the following advantages.

Using the method described in this specification allows for swift improvements in the manufacturing of the biologic pharmaceutical. By repeatedly selecting different control settings and measuring the impact of the control settings on the quality of the biologic pharmaceutical, a control system is able to generate a causal model that models the causal relationships between control settings and the quality of the biologic pharmaceutical more quickly and more accurately than other prior art control systems.

The control system is also able to take into account characteristics of the environment that are not controllable but that affect the quality of the biologic pharmaceutical. Thus, the causal model is able to independently model the relationship between control settings and the quality of the biologic pharmaceutical for various configurations of environment characteristics so that the quality of the biologic pharmaceutical can be less vulnerable to changes in those characteristics.

In some implementations, the control system can continue to operate and use the causal model to select control settings for manufacturing the biologic pharmaceutical. Thus, the system is able to continuously update the causal model while also exploiting the causal model to optimize the quality of the biologic pharmaceutical.

BRIEF DESCRIPTION OF THE DRAWINGS

Like reference numbers and designations in the various drawings indicate like elements.

DETAILED DESCRIPTION

Figure 1A:
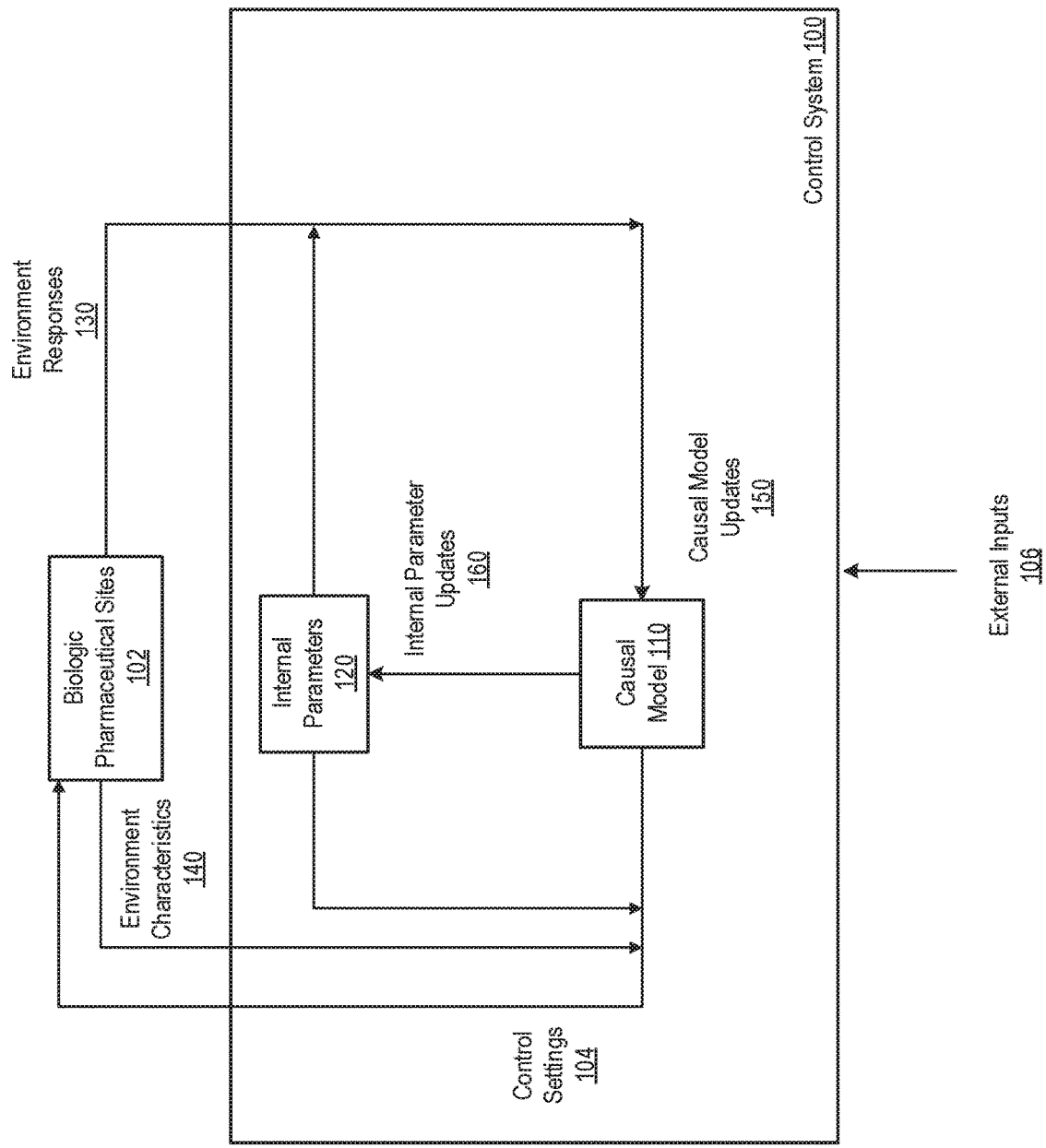
FIG. 1A shows a control system that selects control settings that are applied to biologic pharmaceutical sites.

This specification generally describes a control system that controls an environment as the environment changes states. In particular, the system controls the environment in order to determine causal relationships between control settings for the environment and environment responses to the control settings. In particular, the environment is one or more biologic pharmaceutical sites. A biologic pharmaceutical site is a location where a biologic pharmaceutical is manufactured, e.g. a manufacturing plant or a purification plant for the biologic pharmaceutical. Here, a biologic pharmaceutical is defined as any pharmaceutical drug product manufactured in, extracted from, or semisynthesized from biological sources, e.g. vaccines, blood components, gene therapies, or living cells used in cell therapy. The system selects control settings for manufacturing, including purifying, a batch of the biologic pharmaceutical at the sites. The environment responses are a measure of a quality of the biologic pharmaceutical manufactured using the input settings selected by the system.

For example, the measure of the quality of the biologic pharmaceutical for which causal relationships are being determined can include (i) sensor readings or other environment measurements that reflect the state of the manufactured biologic pharmaceutical, (ii) a performance metric, e.g., a figure of merit or an objective function, that measures the performance of the control system based on environment measurements, or (iii) both.

In particular, the control system repeatedly selects control settings that each include respective settings for each of a set of controllable elements of the biologic pharmaceutical sites. Generally, the selection of different control settings results in differences in system performance, i.e., in different values of the environment responses.

More specifically, by repeatedly selecting control settings and measuring the impact of the control settings on the measure of the quality of the biologic pharmaceutical, the control system updates a causal model that models the causal relationships between control settings and the environment responses, i.e., updates maintained data that identifies causal relationships between control settings and system performance.

While the causal model is referred to as a "causal model," the model can, in some implementations, be made up of multiple causal models that each correspond to different segments of the environment, i.e., to segments of the environment that share certain characteristics.

In some implementations, the control system can continue to operate and use the causal model to select control settings for the biologic pharmaceutical sites. In other implementations, once certain criteria are satisfied, the control system can provide the causal model to an external system or can provide data displaying the causal relationships identified in the causal model to a user for use in controlling the biologic pharmaceutical sites. For example, the criteria can be satisfied after the system has controlled the biologic pharmaceutical sites for a certain amount of time or has selected settings a certain number of times. As another example, the criteria can be satisfied when the causal relationships identified in the maintained data satisfy certain criteria, e.g., have confidence intervals that do not overlap.

While updating the causal model, the system repeatedly selects different control settings and measures the impact of each possible control setting on the measure of the quality of the biologic pharmaceutical manufactured using the control settings based on internal parameters of the control system and on characteristics of the biologic pharmaceutical sites.

In other words, the internal parameters of the control system define both (i) how the system updates the causal model and (ii) how the system determines which control settings to select given the current causal model. While updating the causal model, the control system also repeatedly adjusts at least some of the internal parameters as more environment responses become available to assist in identifying causal relationships.

FIG. 1A shows a control system 100 that selects control settings 104 that are applied to biologic pharmaceutical sites 102. Each control setting 104 defines a setting for each of multiple controllable elements of the biologic pharmaceutical sites 102. Generally, the controllable elements of the biologic pharmaceutical sites 102 are those elements that can be controlled by the system 100 and that can take multiple different possible settings.

The control settings 104 can include settings related to steps for processing the biologic pharmaceutical. For example, the control settings 104 can include an ordering of the processing steps, a time spent in a given processing step, and/or a choice of parameters for a given processing step. The control system 100 can also dictate a time spent in one or more subprocesses of a given processing step.

The control settings 104 can also include settings related to a chemical composition of a given substance. The substance can be the biologic pharmaceutical itself, or it can be any other substance used during the manufacturing of the biologic pharmaceutical. For example, the control settings 104 can include a selection of a nutrient media, an ion exchange resin, an affinity chromatography matrix, a polymer, a wash buffer, and/or an elution buffer.

The control settings 104 can also include settings related to physical control during manufacturing, i.e. controlling the environment and parameters of the manufacturing process. For example, the control settings 104 can include a time of manufacturing and/or a time of purification of the biologic pharmaceutical. The control system 100 can also dictate a temperature during manufacturing and/or purification, a humidity during manufacturing and/or purification, or a flow rate used during manufacturing and/or purification. The control settings 104 can also include a g-force used during manufacturing, a measure of magnetism used during manufacturing, a measure of electricity used during manufacturing, and/or a measure of agitation used during manufacturing.

The control settings 104 can also include settings related to purifying the biologic pharmaceutical. In these cases, the purification process can come after a separate manufacturing process, during a manufacturing process, or by itself, i.e. the given biologic pharmaceutical site exclusively purifies the biologic pharmaceutical. The control system 100 can select the method by which the biologic pharmaceutical is purified, e.g. the control settings can include a selection of electrostatic interactions, hydrophobic interactions, hydrophilic interactions, affinity chromatography, and/or size exclusion chromatography.

During operation, the control system 100 repeatedly selects control settings 104 and monitors environment responses 130 to the control settings 104. The environment responses 130 can be measured using one or more measures of quality of the batch of the biologic pharmaceutical manufactured using the control settings 104. For example, the measures of quality can include a yield of the batch, a measure of an activity of the batch, a measure of an efficacy of the batch, and/or a measure of impurities in the batch. The responses can also include a measure of a viability of transfected cells or a measure of transfection efficiency, if transfection is part of the manufacturing process of the biologic pharmaceutical. The measures of quality can also include a measure of monodispersion, e.g. a dispersion of non-aggregating proteins, and/or a cell density.

As a particular example, the measures of quality of the batch of the biologic pharmaceutical can include a measure of a purity of the biologic pharmaceutical. Here, the purity of the biologic pharmaceutical can include a measure of host cell protein impurity, a measure of DNA impurity, a measure of RNA impurity, and/or a measure of host cell metabolite impurity.

The system can compute a performance metric for the environment responses 130, i.e. can compute a single value that represents the performance of the system in controlling the environment to maximize the quality of the biologic pharmaceutical. An example performance metric that combines all of the measures of quality used by the system is a weighted sum of the values of the chosen measures of quality.

As another example, the performance metric can be a weighted sum of, for each of the measures of quality, a difference between the measure of quality and a baseline or desired value for the measure of quality, i.e., so that the system tries to minimize deviation outside of acceptable values for each of the measures of quality. Another example of such a performance metric is a weighted sum of, for each of the measures of quality, a function that is zero if the measure of quality is within an acceptable range, and is equal to the distance from the measure of quality to the closest end point of the acceptable range if the measure of quality is outside the acceptable range.

The system 100 also monitors the characteristics 140 of the environment 102. Generally, the characteristics 140 can include any data characterizing the environment that may modify the effect that control settings 104 have on environment responses 130 but that are not accounted for in the control settings, i.e., that are not controllable by the control system 100. For example, the environment characteristics 140 of the biologic pharmaceutical sites 102 can include a humidity during manufacturing, an external temperature during manufacturing, and/or a level of light during manufacturing, when the respective measure is not adjustable by the biologic pharmaceutical sites 102. Note that in some cases, these measures might be able to be controllable by the biologic pharmaceutical sites 102, e.g. if the sites 102 can adjust the lighting within the sites. In these cases, the adjustable measures would be included as control settings rather than environment characteristics 140.

The system 100 uses the environment responses 130 to update a causal model 110 that models causal relationships between control settings and the environment responses, i.e., that models how different settings for different elements affect values of the environment responses.

In particular, the causal model 110 measures, for each controllable element of the biologic pharmaceutical sites 102 and for each different type of environment response, the causal effects of the different possible settings for the controllable element on the environment response and the current level of uncertainty of the system about the causal effects of the possible settings.

As a particular example, the causal model 110 can include, for each different possible setting of a given controllable element and for each different type of environment response, an impact measurement that represents the impact of the possible setting on the environment response relative to the other possible settings for the controllable element, e.g., a mean estimate of the true mean effect of the possible setting, and a confidence interval, e.g., a 95% confidence interval, for the impact measurement that represents the current level of system uncertainty about the causal effects.

Thus, the system computes confidence intervals that specify, for example, the 95% upper and lower bound of the impact of the control setting on system performance. Specifically, this allows the system to identify when the selection of different control settings results in (clinically) significant or insignificant differences. The system can refrain from testing controllable elements that do not result in significant differences. For example, to the extent that the upper and lower bounds of the confidence intervals show that even the largest effects would not result in a clinically meaningful difference, and to the extent that there is a cost to continuing to test/explore that controllable element, the system could seek authorization to remove that control setting. For a clinical example, imagine a confidence interval about some control setting on Systolic blood pressure shows the impact of the setting is plus/minus 0.02 points. To the extent that there is any cost, e.g., health-related or otherwise, on continuing to experiment on that setting, the system could seek authorization to stop experimenting as the cost of experimenting would exceed any benefit that a 0.02 reduction in pressure would have on the probability of a cardiac event.

Prior to beginning to control the biologic pharmaceutical sites 102, the control system 100 receives external inputs 106. The external inputs 106 can include data received by the control system 100 from any of a variety of sources. For example, the external inputs 106 can include data received from a user of the system, data generated by another control system that was previously controlling the biologic pharmaceutical sites 102, data generated by a machine learning model, or some combination of these.

Generally, the external inputs 106 specify at least (i) initial possible values for the settings of the controllable elements of the biologic pharmaceutical sites 102 and (ii) which environment responses the control system 100 tracks during operation.

For example, the external inputs 106 can specify that the control system 100 needs to track measurements for certain sensors of the biologic pharmaceutical sites, a performance metric, i.e., a figure of merit or other objective function that is derived from certain sensor measurements, to be optimized by the system 100 while controlling the biologic pharmaceutical sites, or both.

The control system 100 uses the external inputs 106 to generate initial probability distributions ("baseline probability distributions") over the initial possible setting values for the controllable elements. By initializing these baseline probability distributions using external inputs 106, the system 100 ensures that settings are selected that do not violate any constraints imposed by the external data 106 and, if desired by a user of the system 100, do not deviate from historical ranges for the control settings that have already been used to control the biologic pharmaceutical sites 102. For example, if there are certain ranges of the control settings that are known to be unsafe for the biologic pharmaceutical sites 102, then the external data 106 can define those ranges so that the system 100 never selects control settings within the unsafe ranges.

The control system 100 also uses the external inputs 106 to initialize a set of internal parameters 120, i.e., to assign baseline values to the set of internal parameters. Generally, the internal parameters 120 define how the system 100 selects control settings given the current causal model 110, i.e., given the current causal relationships that have been determined by the system 100 and the system uncertainty about the current causal relationships. The internal parameters 120 also define how the system 100 updates the causal model 110 using received environment responses 130.

As will be described in more detail below, the system 100 updates at least some of the internal parameters 120 while updating the causal model 110. That is, while some of the internal parameters 120 may be fixed to the initialized, baseline values during operation of the system 100, the system 100 repeatedly adjusts others of the internal parameters 120 during operation in order to allow the system to more effectively measure and, in some cases, exploit causal relationships.

In particular, in order to control the biologic pharmaceutical sites, during operation, the system 100 repeatedly identifies procedural instances within the biologic pharmaceutical sites based on the internal parameters 120.

Each procedural instance is a collection of one or more entities within the biologic pharmaceutical sites that are associated with a time window. An entity within the biologic pharmaceutical sites is a subset, i.e., either a proper subset or an improper subset, of the biologic pharmaceutical sites. In particular, an entity is a subset of the biologic pharmaceutical sites for which environment responses can be obtained and which can be impacted by applied control settings.

For example, when the biologic pharmaceutical sites include multiple physical entities from which sensor measurements can be obtained, a given procedural instance can include a proper subset of the physical entities to which a set of control settings will be applied. The number of subsets into which the entities within the biologic pharmaceutical sites can be divided is defined by the internal parameters 120.

In particular, how the system 100 divides the entities into subsets at any given time during operation of the system is defined by internal parameters that define the spatial extent of the control settings applied by the system for the instance. The spatial extent of an instance identifies the subset of the environment that is assigned to the instance, i.e., such that environment responses that are obtained from that subset will be associated with the instance.

For example, a procedural instance can include one or more machines that operate using the control settings 104; in these cases, the spatial extent can define the number and type of machines in the procedural instance. The system 100 would obtain the environment responses to the selected control settings for the given group of machines. For example, as described above, the system 100 can select control settings related to a measure of agitation applied by a machine, and then the system 100 can track selected measures of quality of the batch of the biologic pharmaceutical that was processed by the machine using the selected measure of agitation.

The length of the time window associated with the entities in any given procedural instance is also defined by the internal parameters 120. In particular, the time window that the system assigns to any given procedural instance is defined by internal parameters that define the temporal extent of the control settings applied by the system. This time window, i.e., the temporal extent of the instance, defines which future environment responses the system 100 will determine were caused by control settings that were selected for the procedural instance.

Because the internal parameters 120 change during operation of the system 100, the instances generated by the system 100 may also change. That is, the system can modify how the procedural instances are identified as the system changes the internal parameters 120.

The system 100 then selects settings for each instance based on the internal parameters 120 and, in some cases, on the environment characteristics 140.

In some cases, i.e., when the system 100 is exploring the space of possible settings, the system 100 selects the settings for all of the instances based on the baseline probability distributions.

In other cases, i.e., when the system 100 is exploiting the causal relationships that have already been determined to optimize an objective function, the system 100 selects the settings for some of the instances ("hybrid instances") using the current causal model 110 while continuing to select the settings for others of the instances ("baseline instances") based on the baseline probability distributions. More specifically, at any given time during operation of the system 100, the internal parameters 120 define the proportion of hybrid instances relative to the total number of instances.

The system 100 also determines, for each instance, which environment responses 130 will be associated with the instance, i.e., for use in updating the causal model 110, based on the internal parameters 120.

The system 100 then sets the settings 104 for each of the instances and monitors environment responses 130 to the settings that are selected for the instances. The system 100 maps the environment responses 130 to impact measurements for each instance and uses the impact measurements to determine causal model updates 150 that are used to update the current causal model 110.

In particular, the system determines, based on the internal parameters 120, which historical procedural instances (and the environment responses 130 associated with the instances) should be considered by the causal model 110, and determines the causal model updates 150 based only on these determined historical procedural instances. Which historical procedural instances are considered by the causal model 110 is determined by a set of internal parameters 120 that define a data inclusion window. The data inclusion window specifies, at any given time, one or more historical time windows during which a procedural instance must have occurred in order for the results for that procedural instance, i.e., the environment responses 130 associated with that procedural instance, to be considered by the causal model 110.

For those internal parameters that are being varied by the system 100, the system 100 periodically also updates 160 the data that is maintained by the system 100 for those internal parameters based on the causal model 110. In other words, as the causal model 110 changes during operation of the system 100, the system 100 also updates the internal parameters 120 to reflect the changes in the causal model 110. In cases where the system 100 assigns some control settings to exploit the current causal model 110, the system 100 can also use the difference between system performance for "hybrid" instances and "baseline" instances to determine the internal parameter updates 160.

Figure 1B:
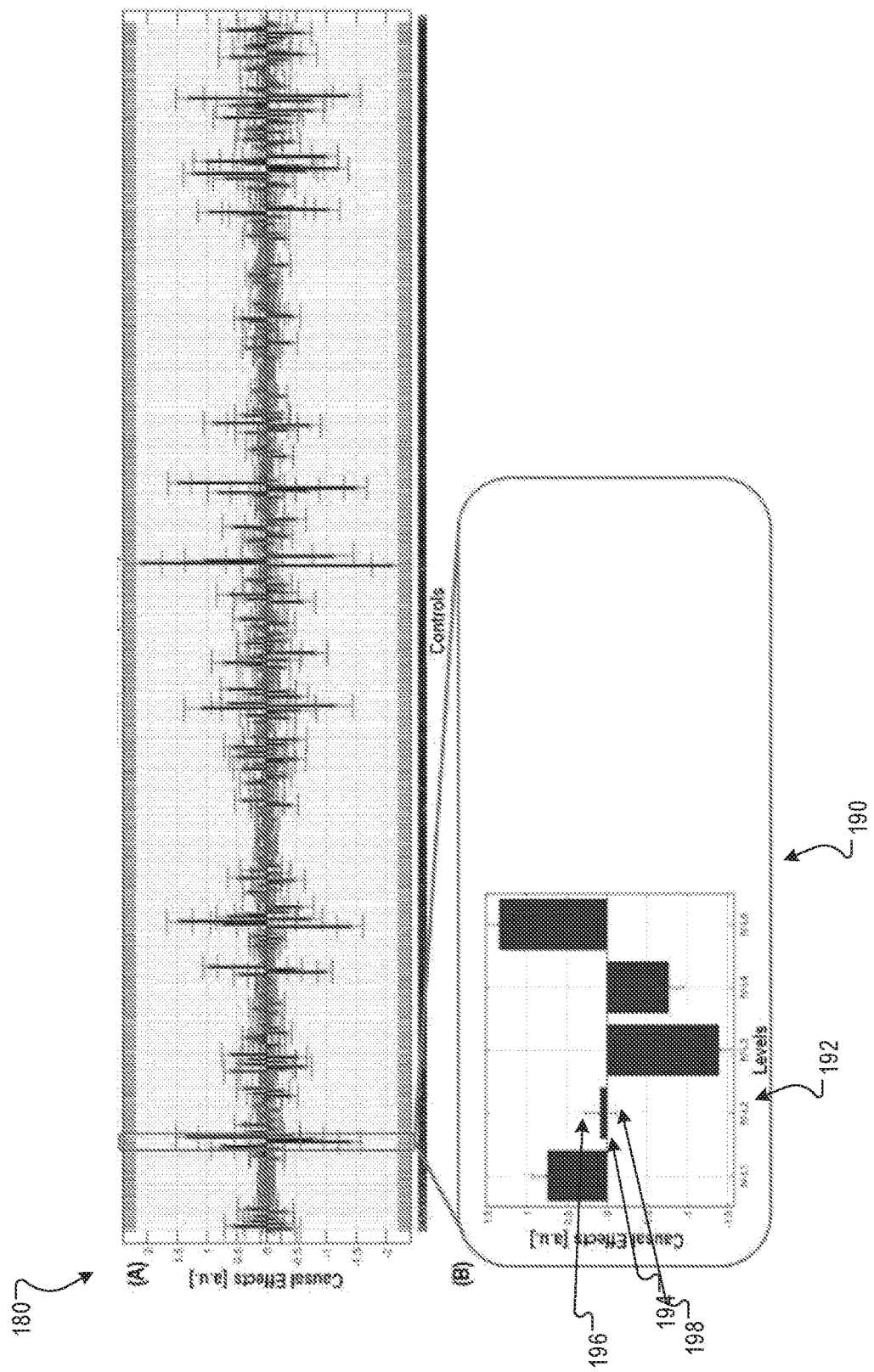
FIG. 1B shows data from an example causal model.

FIG. 1B shows data from an example causal model. In particular, in the example of FIG. 1B, the causal model is represented as a chart 180 that shows control settings, i.e., different possible settings for different controllable elements, on the x axis and causal effects for the control settings on the y axis. In particular, for each possible setting of each controllable element, the causal model depicts an impact measurement and confidence interval around that impact measurement.

These causal relationships are shown in more detail for a particular controllable element 192 in an element-specific chart 190. The element-specific chart 190 shows that there are five possible settings for the controllable element 192, with possible settings being referred to as levels in the chart 190. For each of the five settings, the chart includes a bar that represents the impact measurement and a representation of the confidence interval around the bar as error bars around the impact measurement. Thus, the information in the causal model for any given setting for a controllable element includes an impact measurement and a confidence interval around that impact measurement. For example, for the second setting 192 (denoted as IV-LV2 in the Figure), the chart 190 shows a column 194 that indicates the impact measurement for the second setting, an upper bar 196 above the top of the column 194 that shows the upper limit of the confidence interval for the second setting, and a lower bar 198 below the top of the column 194 that shows the lower limit of the confidence interval for the second setting.

While FIG. 1B shows a single causal model, it will be understood from the description below that the system can maintain and update multiple different causal models for any given controllable element—one for each cluster of procedural instances.

Figure 2:
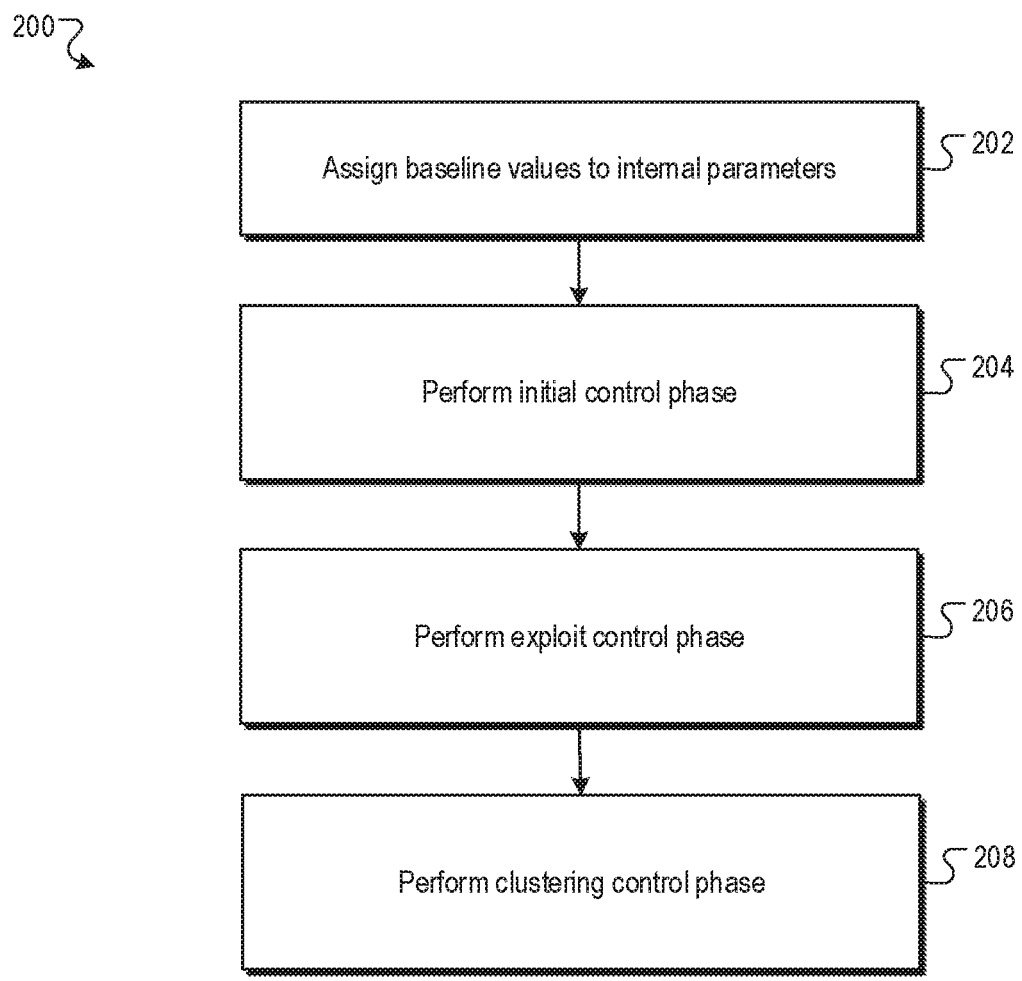
FIG. 2 is a flow diagram of an example process for controlling an environment.

FIG. 2 is a flow diagram of an example process 200 for controlling an environment. For convenience, the process 200 will be described as being performed by a system of one or more computers located in one or more locations. For example, a control system, e.g., the control system 100 of FIG. 1, appropriately programmed, can perform the process 200.

The system assigns baseline values to a set of internal parameters and baseline probability distributions to each of the controllable elements of the environment (step 202).

In particular, the system receives external data, e.g., from a user of the system or data derived from previous control of the system environment by another system, and then uses the external data to assign the baseline values and to generate the probability distributions. Generally, the external data specifies the initial constraints that the system operates within when controlling the environment.

In particular, the external data identifies the possible control settings for each of the controllable elements in the environment. That is, the external data identifies, for each of the controllable elements in the environment, which possible settings the system can select for the controllable element when controlling the system.

In some cases, the external data can specify additional constraints for possible control settings, e.g., that the settings for certain controllable elements are dependent on the settings for other controllable elements or that certain entities can only be associated with a certain subset of the possible control settings for a given controllable element.

Thus, the external data defines the search space of possible combinations of control settings that can be explored by the system when controlling the environment.

In some implementations, these constraints can change during operation of the system.

For example, the system can receive additional external inputs modifying the possible control settings for one or more of the controllable elements or the ranges of values for the spatial and temporal extents.

As another example, if the system determines that optimal settings for one of the controllable elements or for one of the internal parameters are approaching the boundary of the search space defined by external constraints, e.g., if the impact measurements in the causal model indicate the most optimal settings are those closest to one of the boundaries of the search space, the system can seek authorization to expand the space of possible values for the controllable element or the internal parameter, e.g., from a system administrator or other user of the system.

As yet another example, if the external data specifies that the possible settings for some controllable element can be any value in a continuous range, the system can initially discretize the range in one way and then, once the confidence intervals indicate strongly enough that the optimal values are in one segment of the continuous range, modify the discretization to favor that segment.

As yet another example, if the system determines that a certain controllable element has no causal effect on the environment responses, e.g., if the impact measurements for all possible settings of the controllable element are all likely to be zero, the system can seek authorization to remove the controllable element from being controlled by the system.

The system then generates a baseline (or "prior") probability distribution over the possible control settings for each of the controllable elements of the environment. For example, when the external data specifies only the possible values for a given controllable element and does not assign priorities to any of the possible values, the system can generate a uniform probability distribution over the possible values that assigns an equal probability to each possible value. As another example, when the external data prioritizes certain settings over others for a given controllable element, e.g., based on historical results of controlling the environment, the system can generate a probability distribution that assigns higher probability to the prioritized settings.

The system also assigns baseline values to each of the internal parameters of the system. In particular, the internal parameters of the system include (i) a set of internal parameters that define the spatial extents of the procedural instances generated by the system (referred to as "spatial extent parameters") and (ii) a set of internal parameters that define the temporal extents of the procedural instances generated by the system (referred to as "spatial extent parameters").

In some cases where the system includes multiple entities, the system can maintain separate sets of spatial extent parameters and temporal extent parameters for each of the multiple entities. In other cases where the system includes multiple entities, the system maintains only a single set of spatial and temporal extent parameters that apply to all of the multiple entities. In yet other cases where the system includes multiple entities, the system initially maintains a single set of spatial and temporal extent parameters and, during operation of the system, can switch to maintaining a separate set of spatial extent or temporal extent parameters if doing so results in improved system performance, i.e., if different entities respond to control settings differently from other entities.

Additionally, in some implementations, the system maintains separate sets of temporal extent parameters for different controllable elements.

The system also maintains (iii) a set of internal parameters that define the data inclusion window used by the system (referred to as "data inclusion window parameters"). In some implementations, the system maintains a single set of data inclusion window parameters that applies to all of the controllable elements. In some other implementations, the system maintains a separate set of data inclusion window parameters for each controllable element of the environment, i.e., to allow the system to use different data inclusion windows for different controllable elements when updating the causal model. As will be described in more detail below, in cases where the system has clustered the procedural instances into more than one cluster, the system can either (a) maintain a separate set of data inclusion window parameters per cluster or (b) maintain a separate set of data inclusion window parameters per cluster and per controllable element, i.e., so that different clusters can use different data inclusion windows for the same controllable element.

In implementations where the system exploits the causal model, the internal parameters also include (iv) a set of internal parameters that define the hybrid instance to baseline instance ratio (referred to as "ratio parameters"). In some implementations, the system maintains a single set of ratio parameters that applies to all of the controllable elements. In some other implementations, the system maintains a separate set of ratio parameters for each controllable element of the environment, i.e., to allow the system to use different ratios for different controllable elements when selecting control settings. As will be described in more detail below, in cases where the system has clustered the procedural instances into more than one cluster, the system can either (a) continue to maintain a single set of ratio parameters across all of the clusters, (b) maintain a separate set of ratio parameters per cluster or (c) maintain a separate set of ratio parameters per cluster and per controllable element, i.e., so that different clusters can use different ratios when selecting control settings for the same controllable element.

In implementations where the system clusters the instances into multiple clusters, as will be described below, the internal parameters also include (v) a set of internal parameters that define the current clustering strategy (referred to as "clustering parameters").

Generally, the clustering parameters are or define the hyperparameters of the clustering technique that is used by the system. Examples of such hyperparameters include the cluster size of each cluster, i.e., the number of procedural instances in each cluster, and the environmental characteristics that are used to cluster the procedural instances.

The system maintains a set of clustering parameters for each controllable element. That is, for each controllable element, the system uses different hyperparameters when applying the clustering techniques to generate clusters of procedural instances for that controllable element.

The internal parameters can also optionally include any of a variety of other internal parameters that impact the operation of the control system. For example, the internal parameters may also include a set of internal parameters that define how to update the causal model (e.g. a set of weights, each representing the relative importance of each environment characteristic during propensity matching between procedural instances, which can be used to compute d-scores as described below).

As described above, the system varies at least some of these internal parameters during operation.

For each of set of internal parameters that the system varies while controlling the environment, the system can vary the values using a (i) heuristic-based approach, (ii) by stochastically sampling values to optimize a figure of merit for the internal parameter, or (iii) both.

For any sets of internal parameters that are varied only based on heuristics, the system maintains a single value for the internal parameter and repeatedly adjusts that single value based on the heuristics.

For any sets of internal parameters that are varied by stochastically sampling, the system maintains parameters that define a range of possible values for the internal parameter and maintains a causal model that identifies causal relationships between the possible values for the internal parameter and a figure of merit for the internal parameter. The figure of merit for the internal parameter may be different from the performance metric used in the causal model for the control settings. For at least some of the instances at any given time, the system then selects values from within the range of possible values based on the current causal model.

When the system updates a set of internal parameters using heuristics in addition to through stochastic sampling, the system can update the range of possible values using the heuristics. That is, the range of possible values is updated through the heuristic-based approach, while the causal model for the values within the range at any given time is updated through stochastic sampling.

For any internal parameters that the system does not vary while controlling the environment, the system can either maintain a fixed range of values and a fixed probability distribution over the fixed range of values or a fixed single value that is always the value used during the operation of the system.

Depending on what is included in the external data, the system assigns to each internal parameter a baseline value that is either derived from the external data or is a default value.

For example, the external data generally identifies a range of values for the spatial and temporal extents. For example, when the spatial extent is not fixed and is an internal parameter that can be varied by the system, the external data can specify a minimum and maximum value for the spatial extent. Similarly, when the temporal extent is not fixed and is an internal parameter that can be varied by the system, the external data can specify a minimum and maximum value for the temporal extent.

The system then uses the external data to assign the initial values to the spatial extent parameters so that the parameters define the range of values that is specified in the external data and assigns initial values to the temporal extent parameters so that the parameters define the range of values that is specified in the external data.

For other internal parameters, the system assigns default values. For example, the system can initialize the clustering parameters to indicate that the number of clusters is 1, i.e., so that there is no clustering in the outset of controlling the environment, and can initialize the ratio parameters to indicate that there are no hybrid instances, i.e., so that the system only explores at the outset of controlling the environment. The system can also initialize the data inclusion window parameters to indicate that the data inclusion window includes all historical procedural instances that have been completed.

The system performs an initiation phase (step 204). During the initiation phase, the system selects control settings for the procedural instances based on the baseline probability distributions for the controllable elements and uses the environment responses to update the causal model. That is, so long as no historical causal model was provided as part of the external data, the system does not consider the current causal model when determining which control settings to assign to the procedural instances.

Instead, the system selects control settings using the baseline probability distribution in accordance with an assignment scheme that allows impact measurements, i.e., d-scores, to later be computed effectively. In other words, the assignment scheme selects control settings in a manner that accounts for the blocking scheme that is used by the system to compute impact measurements, i.e., assigns control settings to different procedural instances that allow blocked groups to later be identified in order to compute impact measurements between the blocked groups. The blocking scheme (and, accordingly, the assignment scheme) employed by the system can be any of a variety of schemes that reduce unexplained variability between different control settings. Examples of blocking schemes that can be employed by the system include one or more of double-blind assignment, pair-wise assignment, latin-square assignment, propensity matching, and so on. Generally, the system can use any appropriate blocking scheme that assigns procedural instances to blocked groups based on the current environment characteristics of the entities in the procedural instances.

When one or both of the spatial and temporal extent can be varied by the system, the system varies the spatial extent parameters, the temporal extent parameters, or both, during the initialization phase so that values of the spatial and temporal extents that are more likely to result in sufficiently orthogonal procedural instances are more likely to be selected. A group of instances is considered to be orthogonal if the control settings applied to one of the instances in the group do not affect the environment responses that are associated with any of the other instances in the group.

Selecting control settings and updating the causal model while in the initialization phase is described in more detail below with reference to FIG. 3. Varying the spatial or temporal extent parameters is described in more detail below with FIG. 11.

In some implementations, the system continues in this initialization phase throughout the operation of the system. That is, the system continues to explore the space of possible control settings and compiles the results of the exploration in the causal model.

As an example, the system can continue in this initialization phase when the system is updating a causal model with respect to multiple different environment responses rather than with respect to a single figure of merit or objective function, i.e., when the system does not have a figure of merit or objective function to use when exploiting the causal model.

In some of these implementations, the system continues to explore the space of possible control settings while also adjusting certain ones of the sets of initial parameters based on the causal model, e.g., the spatial extent parameters, the temporal extent parameters, the data inclusion window parameters, the clustering parameters, and so on.

In some other implementations, once the system determines that certain criteria are satisfied, the system begins performing a different phase. In these implementations, during the initialization phase, the system holds certain ones of the internal parameters fixed. For example, the system can hold the data inclusion window parameters fixed to indicate that all historical instances should be incorporated in the causal model. As another example, the system can hold the clustering internal parameters fixed to indicate that no clustering should be performed.

In particular, in these other implementations, once the system determines that the criteria are satisfied, the system can begin performing an exploit phase (step 206).

For example, the system can begin performing the exploit phase once the amount of procedural instances for which environment responses have been collected exceeds a threshold value. As a particular example, the system may determine that the threshold value is satisfied when the total number of such procedural instances exceeds the threshold value. As another particular example, the system can determine that the threshold value is satisfied when the minimum number of environment responses associated with any one possible setting for any controllable element exceeds the threshold value.

Additionally, in some cases the system does not employ an initialization phase and immediately proceeds to the exploit phase, i.e., does not perform step 204.

When a threshold is used, the system can determine the threshold value in any of a variety of ways.

As one example, the system can determine that the threshold value is satisfied when environment responses have been collected for enough instances such that assigning settings for instances based on the causal model results in different settings having different likelihoods of being selected. How to assign likelihoods based on the causal model is described in more detail below with reference to FIG. 5.

As another example, the system can determine the threshold value to be the number of procedural instances that are required for the statistical test that the system performs to determine confidence intervals to yield accurate confidence intervals, i.e., the number of procedural instances that satisfies the statistical assumptions for the confidence computations.

As another example, the system can determine the threshold value to be equal to the number of procedural instances that are required to have the causal model yield the desired statistical power, i.e., as determined by a power analysis.

During the exploit phase, the system selects control settings for some of the procedural instances based on the current causal model while continuing to select control settings for other procedural instances based on the baseline values of the internal parameters.

In particular, the system varies the ratio internal parameters so that the ratio between how many procedural instances should be hybrid instances, i.e., instances for which the control settings are assigned based on the causal model, and how many procedural instances should be baseline instances, i.e., instances for which the control settings are assigned based on the baseline probability distributions, is greater than zero.

Because the system begins designating certain instances as hybrid instances during the exploit phase, the system can begin using the difference in system performance between hybrid instances and explore instances to adjust values of the internal parameters, e.g., the ratio internal parameters, the data inclusion window parameters, and so on.

Selecting control settings, updating the causal model, and updating the internal parameters while in the exploit phase are described in more detail below with reference to FIG. 3.

In some implementations, once the system determines that certain criteria are satisfied, the system begins a clustering phase (step 208). That is, if the system is configured to cluster procedural instances, the system begins the clustering phase once the criteria for clustering are satisfied. If the system is not configured to cluster instances, the system does not cluster procedural instances at any point during operation of the system.

Generally, the system considers clustering to create sub-populations of similar procedural instances. In a real-world situation, different procedural instances across a population might respond differently to different control settings. The optimal control setting for one procedural instance might be suboptimal for another. These differences might affect the distributions of the performance metrics seen across instances. If one control setting is selected for the entirety of the population, a detrimental effect in the overall utility, i.e., the overall performance of the system, may result. To maximize the overall utility across the entire population, the system can cluster the instances into sub-populations, taking their individual characteristics (modelled in their environment characteristics) and their feedback characteristics (modelled in the performance metrics received for control settings) into account. The system selects control settings at the level of these subpopulations.

Depending on the implementation and on the criteria, the system can begin the clustering phase during the initialization phase or during the exploit phase. That is, despite FIG. 2 indicating that clustering is step 208 while the initialization phase and the exploit phase are steps 204 and 206, respectively, the clustering phase overlaps with the initialization phase, the exploit phase, or both.

During the clustering phase, prior to assigning control settings to procedural instances, the system clusters the procedural instances into clusters based on current values of the clustering internal parameters and on the characteristics of the procedural instances. As described above, the clustering internal parameters for any given controllable element define the hyperparameters of the clustering technique that will be used to cluster for that controllable element.

Once the system has begun the clustering phase, at any given time, the system maintains a separate causal model for each cluster. That is, the system identifies separate causal relationships within each cluster. As described above, the system can also maintain separate sets of internal parameters for at least some of the internal parameters for each cluster.

The below description will generally describe that separate sets of ratio parameters and data inclusion window parameters are maintained per cluster and per controllable element. However, it should be understood that, when the system maintains only a single set of some type of parameter per cluster, the described computations only need to be performed once for each cluster and the result of the single computation can be used for each controllable element for the cluster. Similarly, when the system maintains only a single set of some type of parameter for all of the clusters, the described computations only need to be performed once and the result of the single computation can be used for all of the controllable elements in all of the clusters.

During the exploit phase, once clustering has been initiated, within a given cluster the system selects control settings for some of the procedural instances in the cluster based on the current causal model while continuing to select control settings for other procedural instances based on the baseline values of the internal parameters.

The system can employ any of a variety of criteria to determine when to begin clustering, i.e., to determine when the clustering internal parameters can begin to vary from the baseline values that indicate that the total number of clusters must be set to one.

As one example, one criterion may include that sufficient environment responses have been collected, e.g., once the amount of environment responses that have been collected exceeds a threshold value. As a particular example, the system may determine that the threshold value is satisfied when the total number of environment responses exceeds the threshold value. As another particular example, the system can determine that the threshold value is satisfied when the minimum number of environment responses associated with any one possible setting for any controllable element exceeds the threshold value.

As another example, another criterion can specify the system can begin clustering once the system has determined that, for any one of the controllable elements, different environment characteristics impact the causal effects of different control settings for that controllable element differently. As a particular example, this criterion can specify that the system can begin clustering when the d-score distributions for any controllable element are statistically different between any two procedural instances, i.e., that the d-score distributions in a causal model that is based only on the environment responses for one procedural instance is statistically different, i.e., to a threshold level of statistical significance, from the d-score distributions in a causal model that is based only on the environment responses for another procedural instance.

Selecting control settings, updating the causal model, and updating the internal parameters while in the clustering phase are described in more detail below with reference to FIG. 3.

Figure 3:
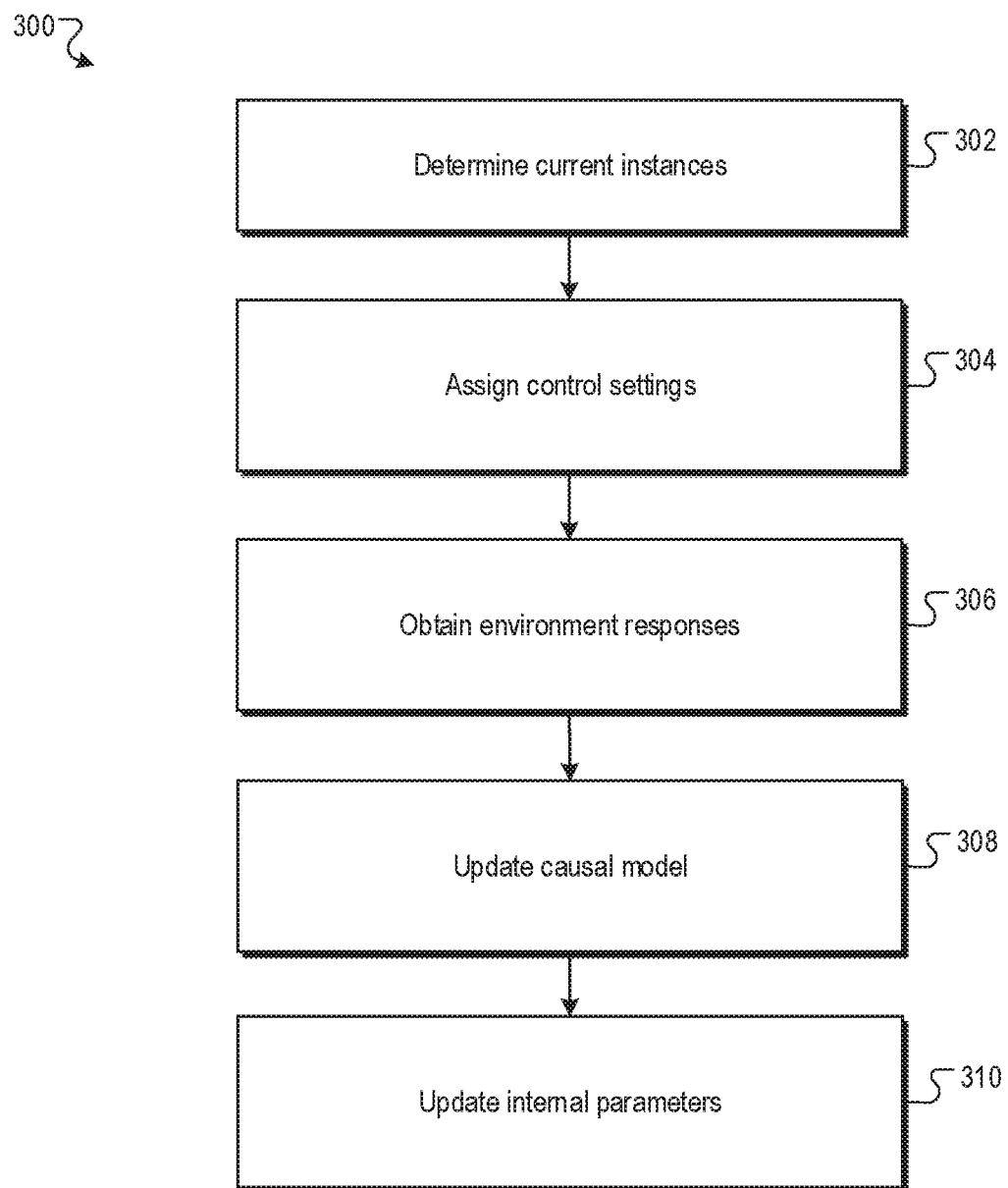
FIG. 3 is a flow diagram of an example process for performing an iteration of environment control.

FIG. 3 is a flow diagram of an example process 300 for performing an iteration of environment control. For convenience, the process 300 will be described as being performed by a system of one or more computers located in one or more locations. For example, a control system, e.g., the control system 100 of FIG. 1, appropriately programmed, can perform the process 300.

The system can repeatedly perform the process 300 to update a causal model that measures causal relationships between control settings and environment responses.

The system determines a set of current procedural instances based on the current internal parameters (step 302). As will be described in more detail below with reference to FIG. 4A, the system determines, based on the current internal parameters, a spatial extent and a temporal extent, e.g., based on how likely different spatial and temporal extents are to result in instances that are orthogonal, and then generates the current procedural instances based on the spatial and temporal extent.

As described above, each procedural instance is a collection of one or more entities within the environment and is associated with a time window. The time window associated with a given procedural instance defines, as described in more detail below, which environment responses the system attributes to or associates with the procedural instance.

In some cases, for each controllable element, the system also determines how long the setting which is selected for the controllable element will be applied as a proportion of the time window associated with the controllable element, e.g., the entire time window, the first quarter of the time window, or the first half of the time window. Generally, the duration for which settings are applied can be fixed to a value that is independent of the time window, can be a fixed proportion of the time window, or the proportion of the time window can be an internal parameter that is varied by the system.

Determining the current set of procedural instances is described in more detail below with reference to FIG. 4A.

In cases where the environment includes only a single physical entity, the current set of instances may contain only one instance. Alternatively, the system can identify multiple current instances, with each current instance including the single physical entity but being separated in time, i.e., by at least the temporal extent for the entity.

The system assigns control settings for each current instance (step 304). The manner in which the system assigns the control settings for any given instance is dependent on which control phase the system is currently performing.

As described above, at the outset of controlling the environment, i.e., before enough information is available to determine causal relationships with any confidence, the system operates in an initialization phase. In the initialization phase, the system selects control settings for instances without considering the current causal model, i.e., the system explores the space of possible control settings. That is, the system selects control settings for the instances in accordance with the baseline probability distributions over the possible control settings for each controllable element.

In some implementations, during the initialization phase the system varies the internal parameters that determine the spatial extents, the temporal extents, or both of the procedural instances in order to identify how likely each possible value for the spatial and temporal extents is to result in instances that are orthogonal to one another.

As described above, in some implementations, the set of control phases includes only the initialization phase and the system continues to operate in this initiation phase throughout, i.e., continues to explore the space of possible control settings while compiling environment responses in order to update the causal model.

In some other implementations, the system shifts into an exploit phase once certain criteria are satisfied. In the exploit phase, the system selects control settings for some of the current instances based on the current causal model, i.e., to exploit the causal relationships currently being reflected in the causal model, while continuing to select control settings for others of the current instances based on the baseline values of the internal parameters.

Additionally, in some implementations, either during the initialization phase or the exploit phase, the system begins performing clustering.

When clustering is being performed, the system clusters the procedural instances into clusters. Within each cluster, the system proceeds independently as described above.

That is, during the initialization phase, the system uses the baseline distributions to select settings independently within each cluster while, during the exploit phase, the system assigns control settings for some of the current instances based on the current causal model independently within each cluster while continuing to select control settings for others of the current instances based on the baseline values of the internal parameters independently within each cluster.

By performing clustering, the system is able to conditionally assign control settings based on (i) the factorial interactions between the impact of the settings on environment responses and the environment characteristics of the instances, e.g., the attributes of the instances that cannot be manipulated by the control system, (ii) the factorial interactions of different independent variables, or (iii) both.

Selecting control settings in the exploit phase with and without clustering is described in more detail below with reference to FIG. 5.

The system obtains environment responses for each of the procedural instances (step 306).

In particular, the system monitors environment responses and determines which environment responses to attribute to which current instance based on the time window associated with each procedural instance.

More specifically, for each procedural instance, the system associates with the procedural instance each environment response that (i) corresponds to the entities in the procedural instance and (ii) is received during some portion of the time window associated with the procedural instance. As a particular example, to limit carryover effects from previous control setting assignments, the system can associate with the procedural instance each environment response that corresponds to the entities in the instance and is received more than a threshold duration of time after the start of the time window, e.g., during the second half of the time window, the last third of the time window, or the last quarter of the time window. In some implementations, this threshold duration of time is fixed. In other implementations, the system maintains a set of internal parameters that define this threshold duration and varies the duration during operation of the system.

The system updates the causal model based on the obtained environment responses (step 308).

Updating the causal model is described in more detail below with reference to FIG. 6.

The system updates at least some of the internal parameters (step 310) based on the current performance of the system, i.e., as reflected in the updated causal model, relative to the baseline performance of the system, or both.

In particular, the system can update any of a variety of the sets of internal parameters based on a heuristic-based approach, by stochastic variation, or both. The heuristic-based approach can include heuristics that are derived from one or more of: the updated causal model, the current performance of the system relative to the baseline performance of the system, or on criteria determined using a priori statistical analyses.

In other words, for each set of internal parameters that the system is able to vary, the system can use one or more of the above techniques to update the set of internal parameters to allow the system to more accurately measure causal relationships.

In some cases, the system constrains certain sets of internal parameters to be fixed even if the system able to vary the internal parameters. For example, the system can fix the data inclusion window parameters and the clustering parameters during the initialization phase. As another example, the system can fix the clustering parameters until certain criteria are satisfied, and then begin varying all of the internal parameters that are under the control of the system during the exploit phase after the criteria have been satisfied.

Updating a set of internal parameters is described in more detail below with reference to FIGS. 8-12.

Generally, the system can perform steps 302-306 with a different frequency than step 308 and perform step 310 with a different frequency than both steps 302-306 and step 310. For example, the system can perform multiple iterations of steps 302-306 for each iteration of step 308 that is performed, i.e., to collect environment responses to multiple different sets of instances before updating the causal model. Similarly, the system can perform multiple different instances of step 308 before performing step 310, i.e., can perform multiple different causal model updates before updating the internal parameters.

Figure 4A:
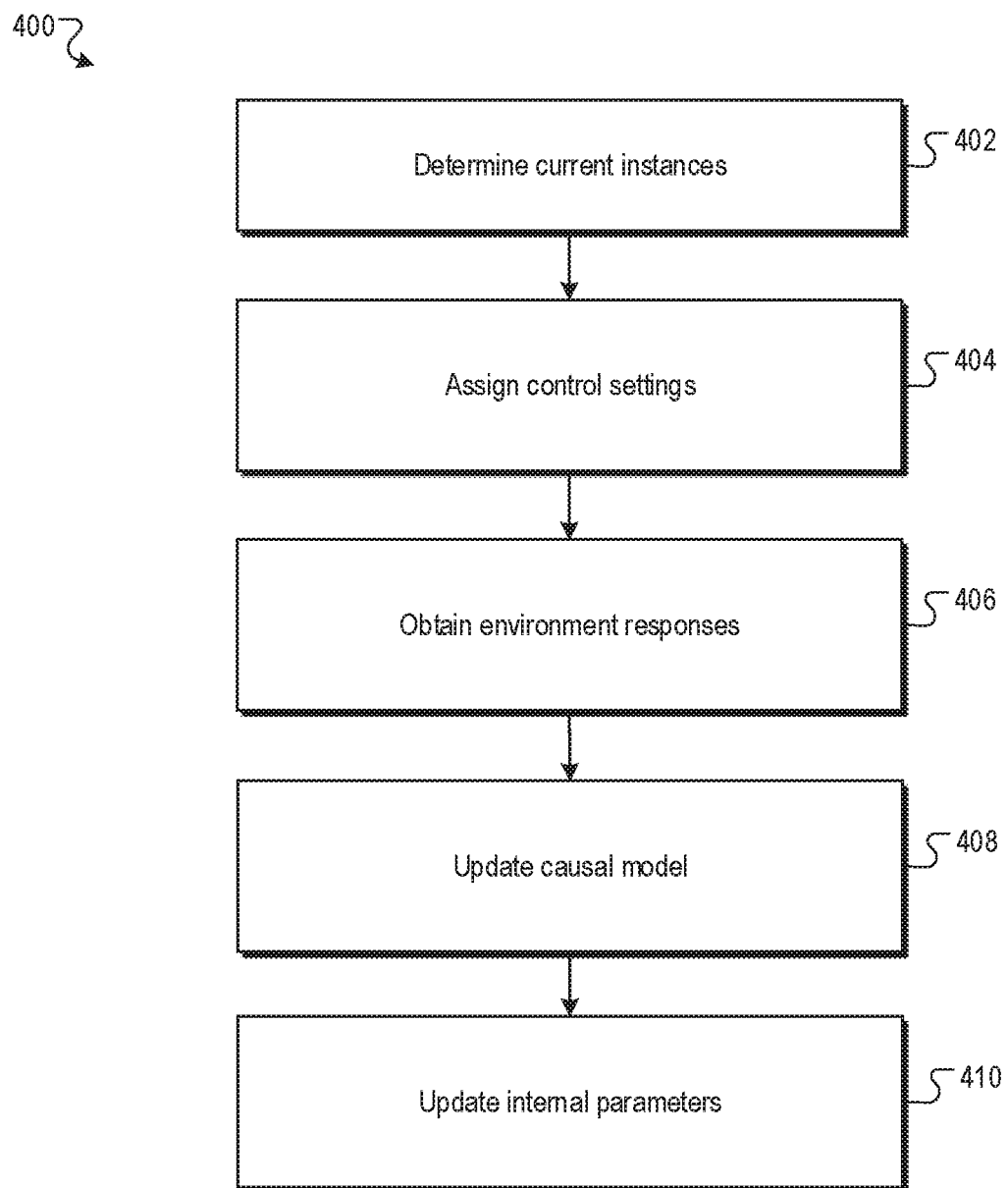
FIG. 4A is a flow diagram of an example process for determining procedural instances.

FIG. 4A is a flow diagram of an example process 400 for determining procedural instances. For convenience, the process 400 will be described as being performed by a system of one or more computers located in one or more locations. For example, a control system, e.g., the control system 100 of FIG. 1, appropriately programmed, can perform the process 400.

The system selects a spatial extent for each of the entities in the environment (step 402). The spatial extent for a given entity defines the segment of the environment that, when controlled by a given set of control settings, impacts the environment responses that are obtained from the given entity. The spatial extent for a given entity is defined by a set of spatial extent parameters, e.g., either a set of spatial extent parameters that is specific to the given entity or a set that is shared among all entities In some implementations, the spatial extent internal parameters are fixed, i.e., are held constant to the same value or are sampled randomly from a fixed range throughout the controlling of the environment. For example, if the environment includes only a single entity, each procedural instance will include the same, single entity. As another example, if the environment includes multiple entities, but there is no uncertainty about which entities are affected by a control setting, the spatial extent parameters can be fixed to a value that ensures that the instances generated will be orthogonal.

When the spatial extent is not fixed and a single value is maintained for the spatial extent parameters (i.e., the spatial extent parameters are updated based on heuristics only), the system selects the current value for the spatial extent parameter for each entity as the spatial extent for the entity. When the spatial extent is not fixed and a range of values is defined by the spatial extent parameters, the system samples a value for the spatial extent from the range currently defined by the spatial extent parameters based on the current causal model for the spatial extent parameters for the entity.

By selecting the spatial extents for the entities, the system defines how many entities are in each procedural instance and which entities are included in each procedural instance. In particular, the system generates the procedural instances such that no procedural instance covers a segment of the environment that is even partially within the spatial extent of an entity in another procedural instance.

Figure 4B:
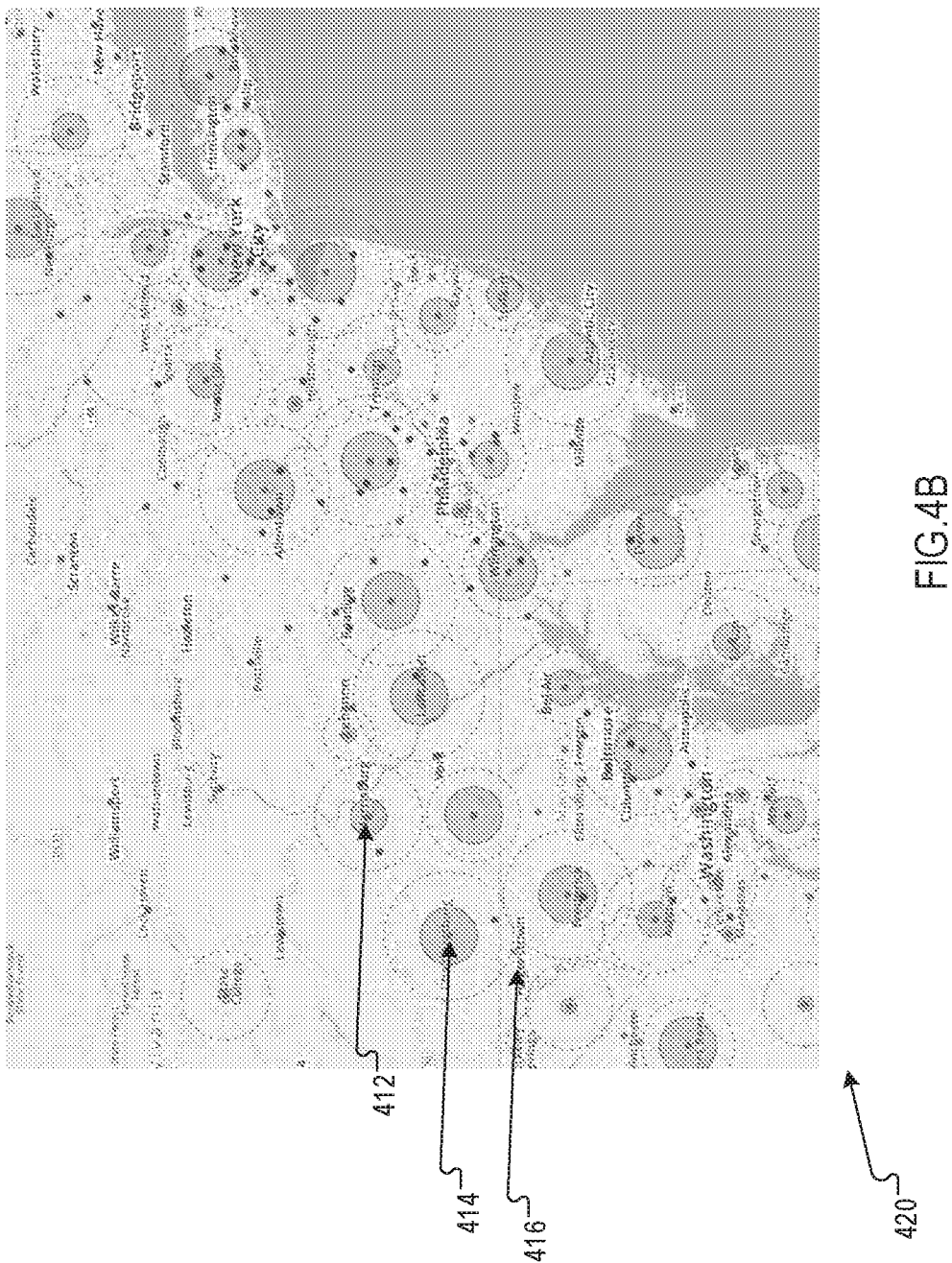
FIG. 4B shows an example of an environment that includes multiple physical entities that are each associated with a spatial extent.

FIG. 4B shows an example of a map 420 of an environment that includes multiple physical entities that are each associated with a spatial extent. In particular, FIG. 4B shows an environment that includes multiple physical entities, represented as dots in the Figure, within a portion of the United States. The spatial extent selected by the system for each entity is represented by a shaded circle. For example, the system may maintain a range of possible radii for each entity and can select the radius of the shaded circle for each entity from the range. As can be seen from the example of FIG. 4B, different entities can have different spatial extents. For example, entity 412 has a different sized shaded circle than entity 414.

As can also be seen from the example of FIG. 4B, the system can also optionally apply additional criteria to reduce the likelihood that the procedural instances are not orthogonal. In particular, the system has also selected for each entity a buffer that extends beyond the spatial extent for the entity (represented as a dashed circle) and has required that no entity in a different instance can have a spatial extent that is within that buffer.

Because of the spatial extents and because of the buffer, certain entities within the environment are not selected as part of a procedural instance in the iteration that is depicted in FIG. 4B. These unselected entities, e.g., entity 416, are represented as dots without shaded or dashed circles. In particular, the system has not selected these entities because their spatial extents intersected with the spatial extent or buffer of another entity that was selected as part of a procedural instance. For entity 416, the entity was not selected because the spatial extent of entity 416 would have intersected with the spatial extent or buffer of entity 414. For example, given the sampled spatial extents and buffers, the system could have selected the spatial extents that would maximize the number of procedural instances that could be included in the current set of instances without violating any of the criteria.

The system selects a temporal extent for each procedural instance or, if different controllable elements have different temporal extents, for each controllable element of each procedural instance (step 404). As described above, the temporal extent defines the time window that is associated with each of the procedural instances or the time windows that are associated with the controllable elements within the procedural instances.

In some cases, the temporal extent can be fixed, i.e., it is known before the operation of the control system to a user of the system which environment responses that are observed for a given entity in the environment should be attributed to the procedural instance that includes that entity. In other cases, the temporal extent can be unknown or be associated with some level of uncertainty, i.e., a user of the system does not know or does not specify exactly how long after a set of settings is applied the effects of that setting can be observed.

In cases where the temporal extent is not fixed, the system samples a value for the temporal extent from the range currently defined by the temporal extent parameters based on the current causal model for the temporal extent parameters. As described above, different entities (and therefore different procedural instances) can have different sets of temporal extent parameters or all of the entities can share the same set of temporal extent parameters.

The system generates procedural instances based on the selected spatial extent and the selected temporal extents (step 406). In other words, the system divides the entities in the environment based on the spatial extent, i.e., so that no entity that is in a procedural instance has a spatial extent (or buffer, if used) that intersects with the spatial extent of another entity that is in a different procedural instance, and associates each procedural instance with the time window defined by the spatial extent for the procedural instance.

Figure 5:
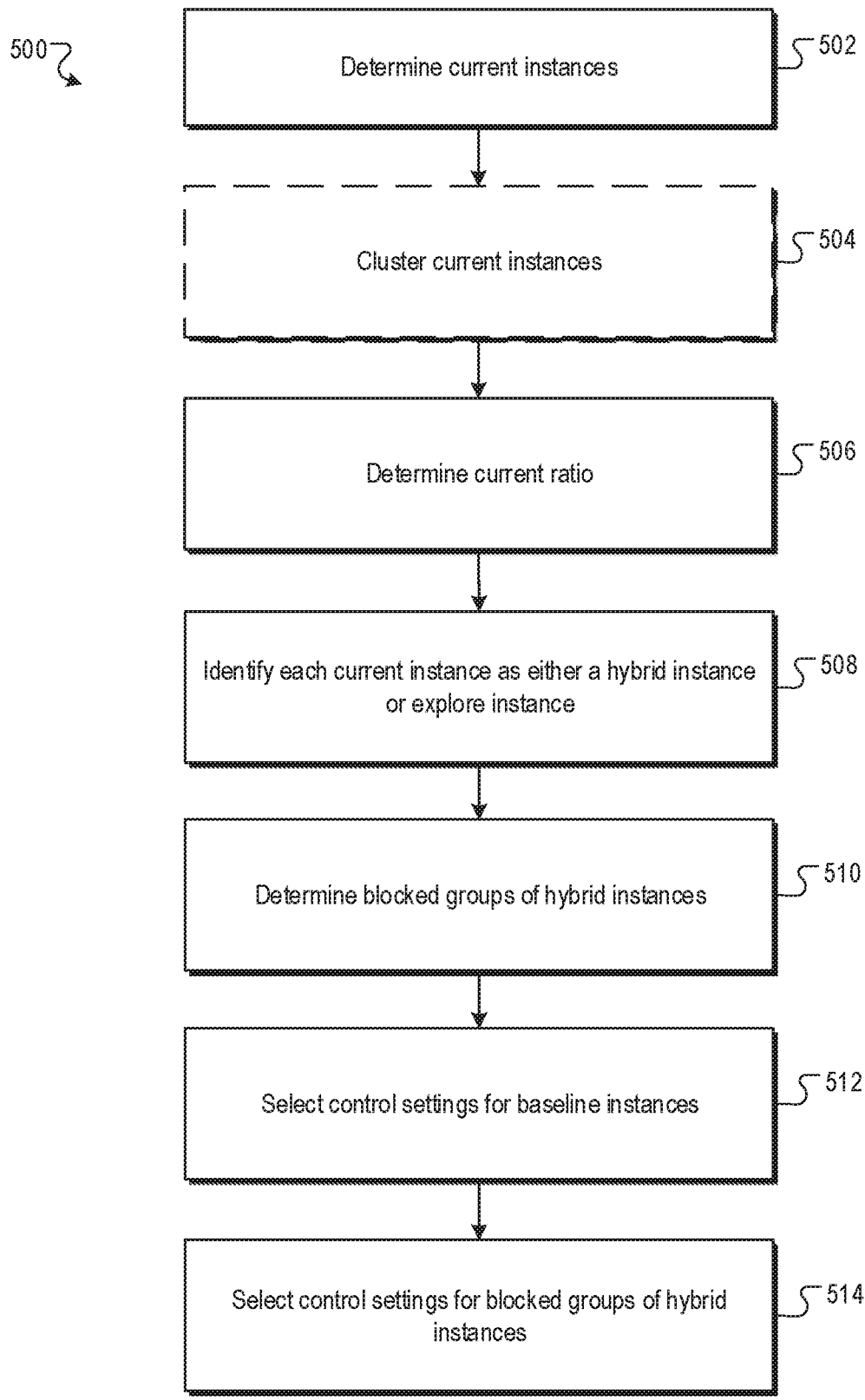
FIG. 5 is a flow diagram of an example process for selecting control settings for the current set of instances.

FIG. 5 is a flow diagram of an example process 500 for selecting control settings for the current set of instances. For convenience, the process 500 will be described as being performed by a system of one or more computers located in one or more locations. For example, a control system, e.g., the control system 100 of FIG. 1, appropriately programmed, can perform the process 500.

The system determines current procedural instances (step 502), e.g., as described above with reference to FIG. 4A.

The system then performs steps 504-514 for each of the controllable elements to select a setting for the controllable elements for all of the current procedural instances.

Optionally, the system clusters the current procedural instances based on the environment characteristics, i.e., generates multiple clusters for the controllable element (step 504). Because the clustering is performed per controllable element, the system can cluster the current procedural instances differently for different controllable elements. Clustering the procedural instances is described below with reference to FIG. 7.

That is, when the system is currently performing the clustering phase, the system first determines the current cluster assignments for the current procedural instances. After the system determines the current cluster assignments, the system performs an iteration of the steps 506-514 independently for each cluster.

When the system is not currently performing the clustering phase, the system does not cluster the current procedural instances and performs a single iteration of the steps 506-514 for all of the current procedural instances.

The system determines a current hybrid to baseline ratio (step 506). In particular, when the set of ratio parameters for the controllable element include only a single value, the system selects the current value of the ratio parameter as the current hybrid to baseline ratio. When the system of ratio parameters for the controllable element defines a range of possible values, the system samples a value for the hybrid to baseline ratio from the current range of possible values defined by the ratio parameters based on the causal model for the set of ratio parameters.

The system identifies each instance as either a hybrid instance for the controllable element or a baseline instance for the controllable element based on the current hybrid to baseline ratio (step 508). For example, the system can assign each instance to be a hybrid instance with a probability that is based on the ratio or can randomly divide up the total number of instances to as closely equal the ratio as possible. Alternatively, when the system is stochastically varying at least one of the internal parameters based on a difference between hybrid instance performance and baseline instance performance, the system may apply an assignment scheme that assigns the instances based on the current ratio and that accounts for the blocking scheme used when computing the causal model that measures the difference between performance, i.e., as described above.

The system selects control settings for the controllable element for the baseline instances based on the baseline values of the internal parameters and in accordance with the assignment scheme (step 512). In other words, the system selects control settings for the baseline instances based on the baseline probability distribution over the possible values for the controllable element determined at the outset of the initialization phase.

The system selects control settings for the hybrid instances based on the current causal model and in accordance with the assignment scheme (step 514).

In particular, the system maps the current causal model to a probability distribution over the possible settings for the controllable element. For example, the system can apply probability matching to map the impact measurements and confidence intervals for the controllable element in the causal model to probabilities.

Generally, the system assigns the control settings based on these probabilities and so that a sufficient number of blocked groups will later be identified by the system when computing d-scores. As a particular example, the system can then divide the hybrid instances into blocked groups (based on the same blocking scheme that will later be used to compute d-scores) and then select control settings within each blocked group in accordance with the probability distribution over the possible settings, i.e., so that each instance in the blocked group is assigned any given possible setting with the probability specified in the probability distribution.

Figure 6:
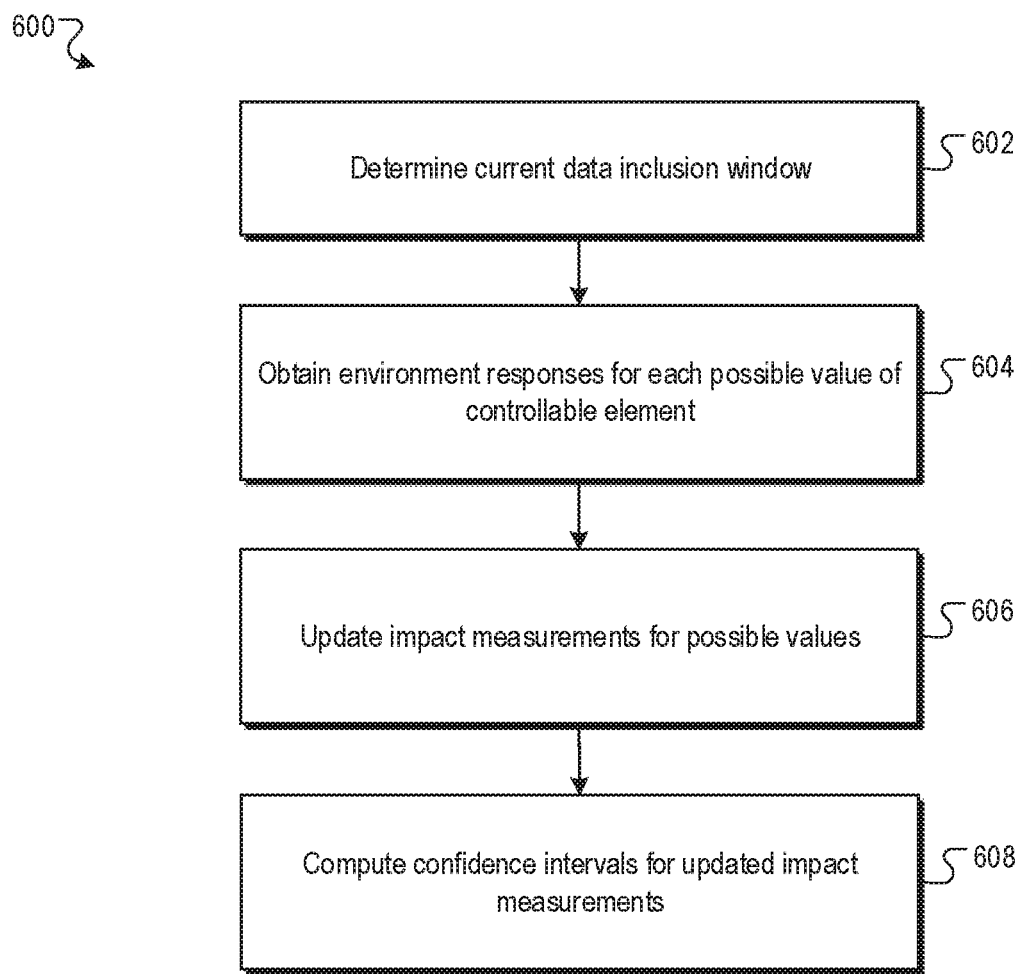
FIG. 6 is a flow diagram of an example process for updating the causal model for a given controllable element and a given type of environment response.

FIG. 6 is a flow diagram of an example process 600 for updating the causal model for a given controllable element and a given type of environment response. For convenience, the process 600 will be described as being performed by a system of one or more computers located in one or more locations. For example, a control system, e.g., the control system 100 of FIG. 1, appropriately programmed, can perform the process 600.

The system can perform the process 600 for each controllable element and for each type of environment response for which the system is maintaining a causal model. For example, when the system is maintaining a causal model that models causal effects for only a single performance metric, the system only performs the process 600 for the performance metric. Alternatively, when the system is maintaining a causal model that models causal effects for multiple different types of environment responses, the system performs the process 600 for each type of environment response, e.g., each different type of sensor reading or measurement.

When the system is currently clustering procedural instances into clusters, the system can perform the process 600 independently for each cluster. That is, the system can independently maintain and update a causal model for each cluster.

The system determines a current data inclusion window for the controllable element (step 602), i.e., based on the current data inclusion window parameters for the controllable element. In particular, when the set of data inclusion window parameters for the controllable element include only a single value, the system selects the current value of the data inclusion window parameter as the current data inclusion window. When the set of data inclusion window parameters for the controllable element defines a range of possible values, the system samples a value for the data inclusion window from the range of values currently defined by the set of data inclusion window parameters. When the data inclusion window parameters are not varied by the system, the system sets the value to the fixed, initial data inclusion window or samples a value from the fixed range of possible values.

The system obtains, for each possible value of the controllable element, the environment responses (step 604) of the given type that have been recorded for instances for which the possible value of the controllable element was selected. In particular, the system obtains only the environment responses for instances that occurred during the current data inclusion window.

The system updates the impact measurements in the causal model based on the environment responses for the possible settings of the controllable element (step 606).

That is, the system determines a set of blocked groups based on a blocking scheme, e.g., one of the blocking schemes described above.

For each blocked group, the system then determines a respective d-score for each possible setting that was selected in any of the instances in the blocked group. Generally, the system computes the impact measurements, i.e., the d-scores, for a given controllable element based on the blocking scheme, i.e., computes d-scores between environment responses for instances that were assigned to the same blocked group.

As a particular example, the impact measurement di for a possible setting i of the controllable element in a blocking scheme that assigns blocked groups to include at least one instance having each possible setting may satisfy:

$$d\_i = x\_i - (\Sigma\_{(j \neq i)} x\_j)/(N-1),$$

where $x\_i$ is the environment response of the given type for the instances within the blocked group where the setting i has been selected, the sum is over all of the possible settings except i, and N is the total number of possible settings.

As another particular example, the impact measurement di for a possible setting i of the controllable element in a blocking scheme that assigns pairs of instances to blocked groups may satisfy:

$$d\_i = x\_i - x\_(i+1).$$

where $x\_i$ is the environment response of the given type for the instance within the blocked group where the setting i was selected and $x\_(i+1)$ is the environment response of the given type for the instance within the blocked group where the setting i+1 was selected, where the setting i+1 is the immediately higher possible setting for the controllable element. For the highest setting for the controllable element, the setting i+1 can be the lowest setting for the controllable element.

As yet another particular example, the impact measurement di for a possible setting i of the controllable element in a blocking scheme that assigns pairs of instances to blocked groups may satisfy:

$$d\_i = x\_i - x\_1,$$

where $x\_1$ the environment response of the given type for the instance that has a predetermined one of the possible settings for the controllable element selected.

The system then computes the updated overall impact measurement for a given setting i as the mean of the d-scores computed for the setting i.

In some cases, the d-score calculation can be proportional rather than additive, i.e., the subtraction operation in any of the above definitions can be replaced by a division operation.

The system determines, for each of the possible values of the controllable element, a confidence interval for the updated impact measurement (step 608). For example, the system can perform a t-test or other statistical hypothesis test to construct a p % confidence interval around the updated impact measurement, i.e., around the mean of the d-scores, where p is a fixed value, e.g., 95% or 97.5% or 99%.

In some implementations, the system applies different p values for different controllable elements, e.g., when the external data specifies that different controllable elements have different costs or levels of risk associated with deviating from the baseline probability distribution for the different controllable elements.

In some implementations, the system applies a correction, e.g., a Bonferroni correction, to the confidence intervals in the case where certain settings for the controllable element are associated with different costs of implementation or a higher risk. In particular, in a Bonferroni correction, a correction is applied such that if N confidence intervals are computed for N possible settings of a controllable element and the overall desired confidence level of that element is 95% (i.e. alpha=0.05), then the alpha value used for each individual test to compute a confidence interval is alpha/N. If certain settings are associated with a higher risk or cost of implementation, then a "corrected" alpha value associated with a higher level of confidence may be specified for those settings. This forces the system to accumulate more data before exploiting those settings.

Figure 7:
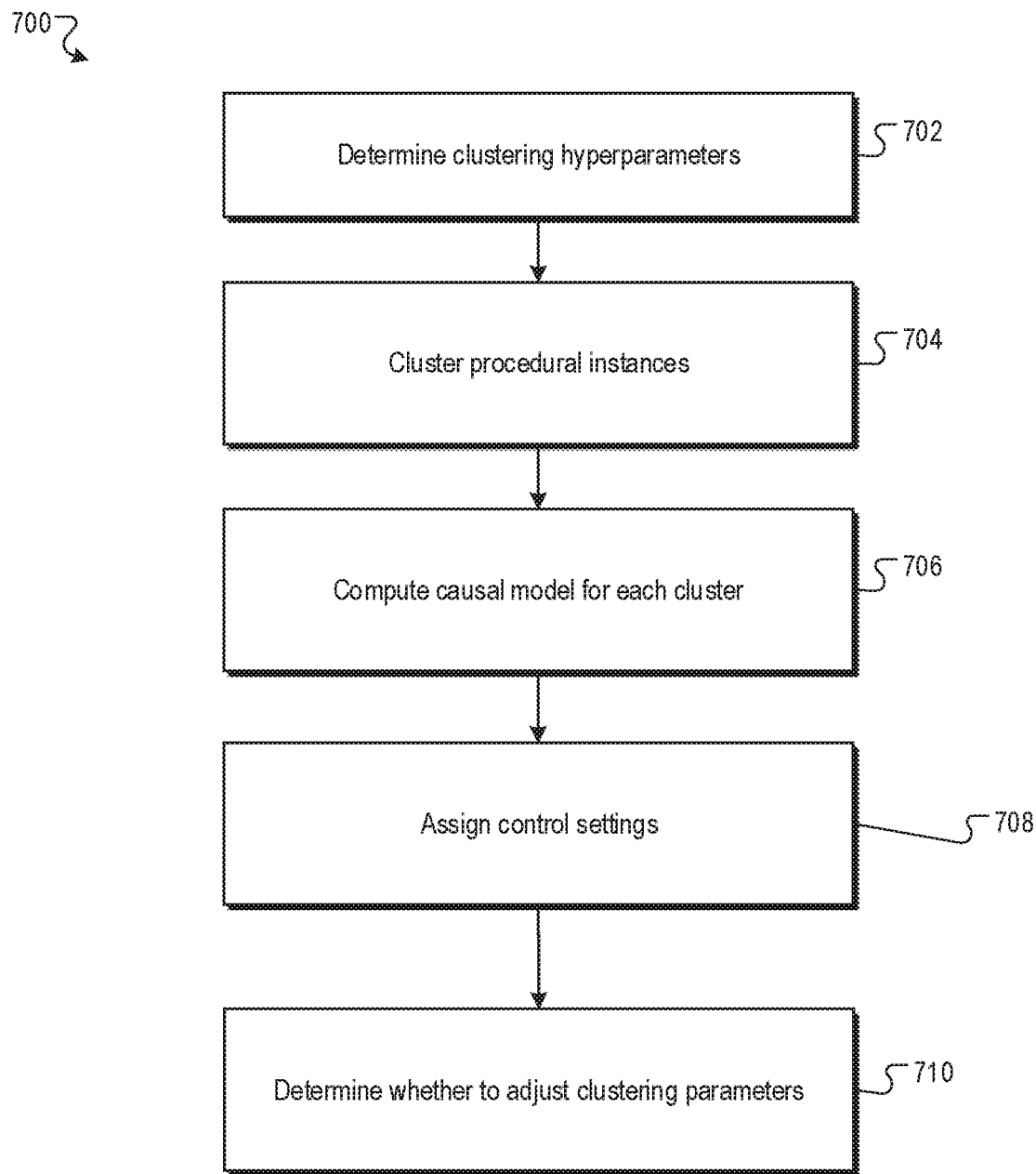
FIG. 7 is a flow diagram of an example process for clustering a set of procedural instances for a given controllable element.

FIG. 7 is a flow diagram of an example process 700 for clustering a set of procedural instances for a given controllable element. For convenience, the process 700 will be described as being performed by a system of one or more computers located in one or more locations. For example, a control system, e.g., the control system 100 of FIG. 1, appropriately programmed, can perform the process 700.

The system selects the current hyperparameters for the clustering technique being used by the system from the clustering parameters for the controllable element (step 702). In particular, each hyperparameter that can be varied by the system is defined by a distinct set of internal parameters. That is, the clustering parameters include a separate set of internal parameters for each hyperparameter that is under the control of the system during operation.

The system can use any of a variety of clustering techniques to perform the clustering. However, the hyperparameters that are varied by the system will generally include hyperparameters for the size of the clusters generated by the clustering technique and, in some cases, the environment characteristics of the instances that are considered by the clustering technique when generating the clusters.

As one example, the system can use a statistical analysis, e.g., a factorial analysis of variance (ANOVA), to generate clustering assignments. In particular, factorial ANOVA is used to find the factors, i.e., the environment characteristics, that explain the largest amount of variance between clusters. That is, as D-scores are computed for each possible control setting, factorial ANOVA can monitor interaction terms between these treatment effects and external factors. As data accumulates and interactions start emerging, factorial ANOVA creates different clusters of instances across space and time where each cluster is representative of distinct external factor states or attributes.

As another example, the system can use a machine learning technique to generate the clustering assignments. As a particular example of a machine learning technique, the system can use decision trees. Decision trees are a classical machine learning algorithm used for classification and regression problems. Decision trees use a recursive partitioning scheme by sequentially identifying the best variable, i.e., the best environment characteristic, to split on using information theoretic functions like the Gini coefficient. As another particular example of a machine learning technique, the system can use conditional inference trees. Like decision trees, conditional inference trees are a recursive binary partitioning scheme. The algorithm proceeds by choosing a sequence of variables to split on, based on a significance test procedure to partition based on the strongest environment characteristic factors. As another particular example, the system can process data characterizing each of the procedural instances and their associated environment characteristics using a machine learning model, e.g., a deep neural network, to generate an embedding and then cluster the procedural instances into the specified clusters based on similarities between the embeddings, e.g., using k means clustering or another clustering technique. As a particular example, the embeddings can be the output of an intermediate layer of a neural network that has been trained to receive data characterizing a procedural instance and to predict the value of the performance metric for the procedural instance.

In some cases, the system can switch clustering techniques as the operation of the system progresses, i.e., as more data becomes available. For example, the system can switch from using a statistical technique or a decision tree to using a deep neural network once more than a threshold amount of procedural instances are available.

The system clusters the instances in the current data inclusion window using the clustering technique in accordance with the selected hyperparameters (step 704).

The system computes a causal model for each cluster (step 706), i.e., as described above with reference to FIG. 6 but using only the instances that have been assigned to the cluster.

The system then assigns control settings for the controllable element independently within each of the clusters based on the computed causal model for the cluster (step 708), i.e., as described above with reference to FIG. 5. In particular, the system clusters each current instance using the clustering technique and then assigns the control settings for a given current instance based on the cluster that the current instance is assigned to and, if the given current instance is not designated a baseline instance, using the causal model computed for the cluster.

The system can then determine whether the clustering parameters need to be adjusted (step 710), i.e., determines if the current values of the clustering parameters are not optimal and, if so, updates the clustering parameters for the controllable element. In particular, during operation, the system updates the clustering parameters to balance two competing goals: (1) pooling instances into clusters such that there is maximum within-cluster similarity of the impact of controllable elements on the performance metric and maximum between-cluster difference in the impact of controllable elements on the performance metric and (2) maximizing the size of clusters in order to have the largest possible within-cluster sample size, to increase the precision of the causal model. The system can accomplish this by adjusting the values using heuristics, using stochastic sampling, or both heuristics and stochastic sampling.

The system can determine whether to change the number of clusters, i.e., to change the value of the clustering parameter for the controllable element, in any of a variety of ways, i.e., based on any of a variety of heuristics.

More generally, as described above, for any given set of internal parameters that are varied by the system, the system can adjust the set of internal parameters in one of three ways: (i) using a heuristic-based approach to adjust a single value, (ii) using stochastic variation to adjust likelihoods assigned to different values in a range of value, or (iii) using a heuristic-based approach to adjust the range of values while using stochastic variation to adjust likelihoods within the current range.

The heuristic-based approach can include heuristics that are based on properties of the current causal model, heuristics that are based on a priori statistical analyses, or both.

In the stochastic variation approach, the system maintains a causal model that measures causal effects between different values within the current range and a figure of merit for the set of internal parameters. The system then maps the causal model to probabilities for the different values and, when required, selects a value for the internal parameter based on the probabilities. As will be described in more detail below, the figure of merit for any given set of internal parameters is generally different from the performance metric that is being measured in the causal model that models causal relationships between the control settings and the performance metric.

Figure 8:
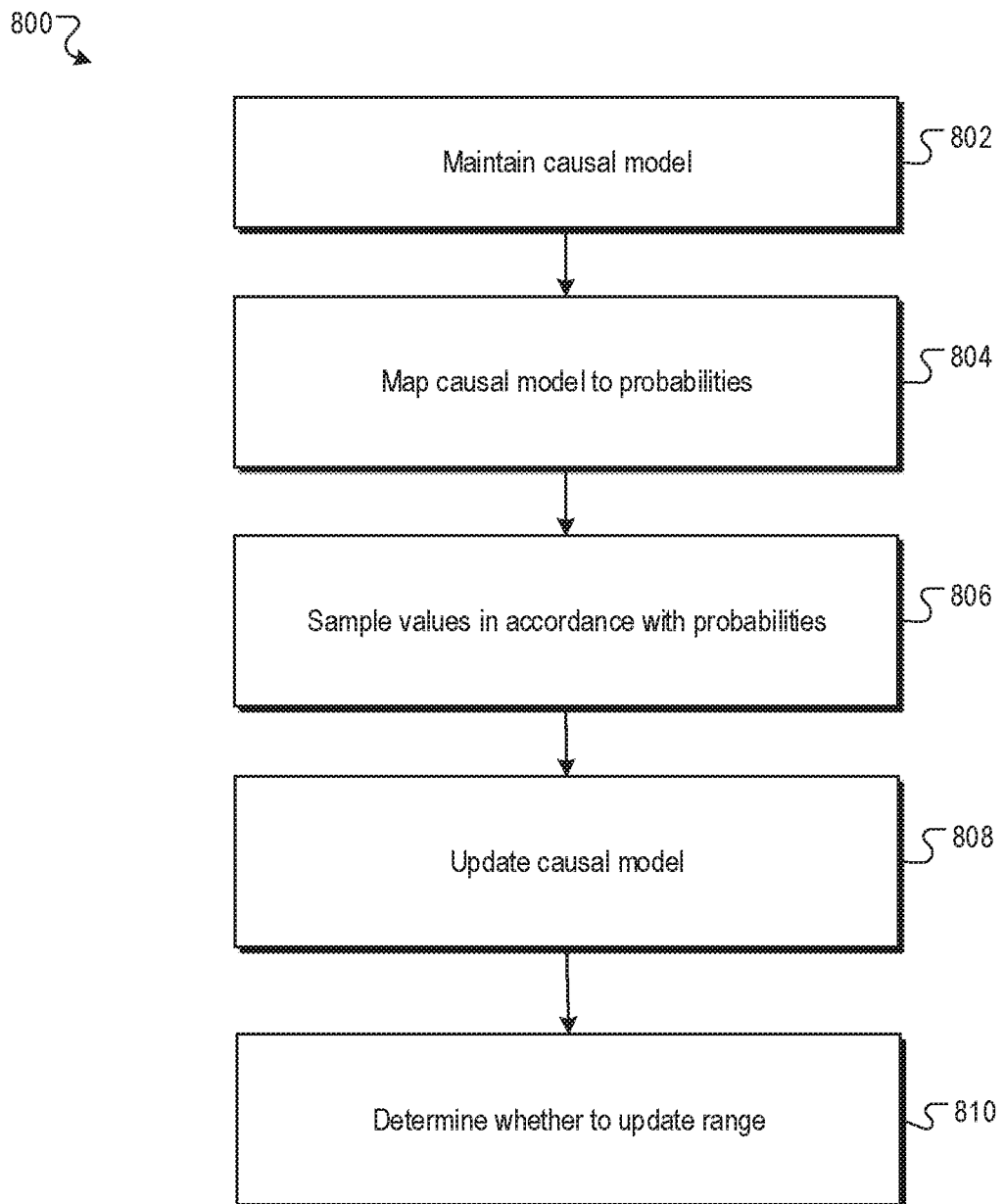
FIG. 8 is a flow diagram of an example process an example process for updating a set of internal parameters using stochastic variation.

FIG. 8 is a flow diagram of an example process 800 for updating a set of internal parameters using stochastic variation. For convenience, the process 800 will be described as being performed by a system of one or more computers located in one or more locations. For example, a control system, e.g., the control system 100 of FIG. 1, appropriately programmed, can perform the process 800.

The process 800 can be performed for any set of internal parameters that is being updated using stochastic variation.

Examples of such internal parameters can include any or all of sets of data inclusion window parameters, sets of clustering parameters, sets of ratio parameters, sets of spatial extent parameters, sets of temporal extent parameters, and so on.

As described above, during the clustering phase and for any set of internal parameters other than the clustering parameters, the system can perform the process 800 independently for each cluster or for each controllable element and for each cluster.

Additionally, in cases where the clustering parameters are varied using stochastic variation, the system can also perform the process 800 independently for each controllable element.

The system maintains a causal model for the set of internal parameters that measures the causal relationships between the different possible values for the internal parameter and a figure of merit for the set of internal parameters (step 802).

For example, the figure of merit for the set of internal parameters can be the difference between the performance of the hybrid instances and the performance of the baseline instances. In this example, the figure of merit measures the relative performance of the hybrid instances to the baseline instances and the system computes impact measurements, i.e., d-scores, on this figure of merit for different values in the range defined by the internal parameters.

Thus, when computing the causal model for the set of internal parameters, the system proceeds as described above with reference to FIG. 6, except that (i) the possible settings are possible values for the internal parameter and (ii) each xi in the d-score calculation is a difference between (1) a performance metric for a hybrid instance for which the control settings were assigned with the possible value for the internal parameter selected and (2) a performance metric for a corresponding baseline instance.

As another example, the figure of merit for the set of internal parameters can be a measure of the precision of the causal model for the controllable element, e.g., a measure of the width of the confidence intervals for the different settings of the controllable element.

This maintained causal model can be determined based on a data inclusion window for the set of internal parameters. When the set of internal parameters actually are the data inclusion window parameters, the data inclusion windows are different for the different possible values in the current range. When the set of internal parameters are a different set of internal parameters, the data inclusion window can be a separate set of internal parameters that is fixed or that is varied based on heuristics as described below or also based on stochastic variation as described in this figure.

The system maps the causal model to a probability distribution over possible values in the range of values, e.g., using probability matching (step 804). That is, the system maps the impact measurements and the confidence intervals to probabilities for each possible value in the range of values using probability matching or another appropriate technique.

When a value is required to be sampled from the range, the system samples values from the range of possible values in accordance with the probability distribution (step 806). That is, when a value from the range defined by the internal parameters is needed for the system to operate, e.g., to assign a temporal extent to a procedural instance, to assign a data inclusion window to a given controllable element, to determine a hyperparameter for a clustering technique, or to assign a current hybrid to baseline ratio for the current set of instances, the system samples from the range of possible values in accordance with the probability distribution. By sampling the values in this manner, the system ensures that values that are most likely to optimize the figure of merit for the set of internal parameters, e.g., to maximize the delta between hybrid and baseline instances, are sampled more frequently while still ensuring that the space of possible values is explored.

The system computes an update to the causal model (step 808). That is, as new environment responses for new procedural instances are received, the system re-computes the causal model by computing overall impact measurements, i.e., means of d-scores, and confidence intervals around the overall impact measurements. The system can perform this computation in the same manner as the causal model updates described above with reference to FIG. 6, i.e., by selecting blocked groups, computing d-scores within those blocked groups (based on the figure of merit for the set of parameters described above), and then generating the causal model from those d-scores.

By repeatedly performing the process 800, the system can repeatedly adjust the probabilities assigned to the values in the range to favor values that result in a more optimal figure of merit.

For example, when the set of internal parameters is the data inclusion window parameters, maintaining a causal model that models the effect that different data inclusion window values have on hybrid versus baseline performance allows the system to select data inclusion windows that results in more accurate and robust causal models being computed for the controllable element.

As another example, when the set of internal parameters are the spatial or temporal extent parameters, maintaining a causal model that models the effect that different spatial or temporal extent values have on hybrid versus baseline performance allows the system to select spatial or temporal extents that result in orthogonal procedural instances that maximize the hybrid instance performance relative to baseline instance performance.

As another example, when the set of internal parameters define a clustering hyperparameter, maintaining a causal model that models the effect that different hyperparameter values have on hybrid versus baseline performance allows the system to select clustering assignments that maximize the performance of the system, i.e., more effectively identify clustering assignments that satisfy the goals described above with reference to FIG. 7.

In some implementations, the system determines whether to adjust the current range of possible values for the internal parameter (step 810). As described above, the range of possible values for any given internal parameter can be fixed or can be adjusted using heuristics to ensure that the space of possible values that is being explored remains rational throughout the operation of the system.

One example of a heuristic that can be used to adjust the current range of possible values is a heuristic that relies on the shape of the current causal model. In particular, the system can increase the upper bound of the range (or increase both the upper and lower bound of the range) when the impact measurements in the causal model are growing in magnitude as the current upper bound of the range is approached and decrease the lower bound (or decrease both the upper and lower bound) when the impact measurements are growing in magnitude as the current lower bound of the range is approached.

Another example of a heuristic that can be used to adjust the current of possible value is a heuristic that relies on a statistical power analysis.

For example, when the set of internal parameters are a set of clustering parameters that define a cluster size used by the clustering technique, the system can compute a statistical power curve that represents the impact that changes in sample size, i.e., cluster size will have on the width of the confidence intervals the current causal model is reflecting for the controllable element. Given the nature of statistical power curves, the confidence intervals become more precise quickly at the small end of the sample size but, as the sample size increases, each additional increase in sample size results in a disproportionately smaller increase in the precision of the confidence intervals (i.e., disproportionally smaller decrease in the width of the confidence intervals). Thus, exploring larger cluster sizes may lead to very little gain in statistical power and comes with a high risk of not accurately representing the current decision space. To account for this, the system can then constrain the range of the possible cluster sizes to a range that falls between a lower threshold and an upper threshold on the statistical power curve. By constraining the cluster sizes in this way, the system does not explore clusters that are so small as to result in too little statistical power to compute significant confidence intervals. The system also does not experiment with cluster sizes that are unnecessarily large, i.e., cluster sizes that result in small gains in statistical power in exchange for the risk of failing to capture all the potential variation between instances.

As another example, when the set of internal parameters are a set of ratio parameters, the system can perform a statistical power analysis to compute the minimum number of baseline instances that are required to determine, given the current causal model for the ratio parameters, that the hybrid instances outperform the baseline instances with a threshold statistic power. The system can then adjust the lower bound of the range of possible ratio values so that the ratio does not result in a number of baseline instances that is below this minimum number.

As another example of adjusting a range based on heuristics, when the range of temporal extent parameters for the entities in the environment are being updated based on heuristics, the system can maintain for each entity a causal model that measures the causal relationships between (i) the control settings selected at a given control iteration and (ii) the environment responses obtained from the entity at the subsequent control iteration, i.e., at the control iteration immediately after the given control iteration. Because the system is attempting to select temporal extents for entities that ensure that procedural instances are orthogonal, if the temporal extent has been properly selected, this causal model should indicate that the causal effects are likely zero between current control settings and environment responses to subsequent control settings. Thus, the system can determine to increase the lower bound on the range of possible temporal extents if the causal model shows that the confidence intervals for the impact measurements for any of the control settings have more than a threshold overlap with zero.

As another example of adjusting a range based on heuristics, when the range of spatial extent parameters for the entities in the environment are being updated based on heuristics, the system can maintain for each given entity a causal model that measures the causal relationships between (i) the control settings selected at a given control iteration for the procedural instance that includes the given entity and (ii) the environment responses obtained from an adjacent entity to the given entity at the current control iteration. The adjacent entity can be the entity that is closest to the given entity from the entities that are included in the current set of instances for the current control iteration. Because the system is attempting to select spatial extents for entities that ensure that procedural instances are orthogonal, if the spatial extent has been properly selected, this causal model should indicate that the causal effects are likely zero between current control settings for the given entity and environment responses for the adjacent entity. Thus, the system can determine to increase the lower bound on the range of possible spatial extents if the causal model shows that the confidence intervals for the impact measurements for any of the control settings have more than a threshold overlap with zero.

Additional examples of heuristics that can be used to adjust the range of possible values for the data inclusion window and the ratio parameters are described in more detail below with reference to FIG. 12.

Figure 9:
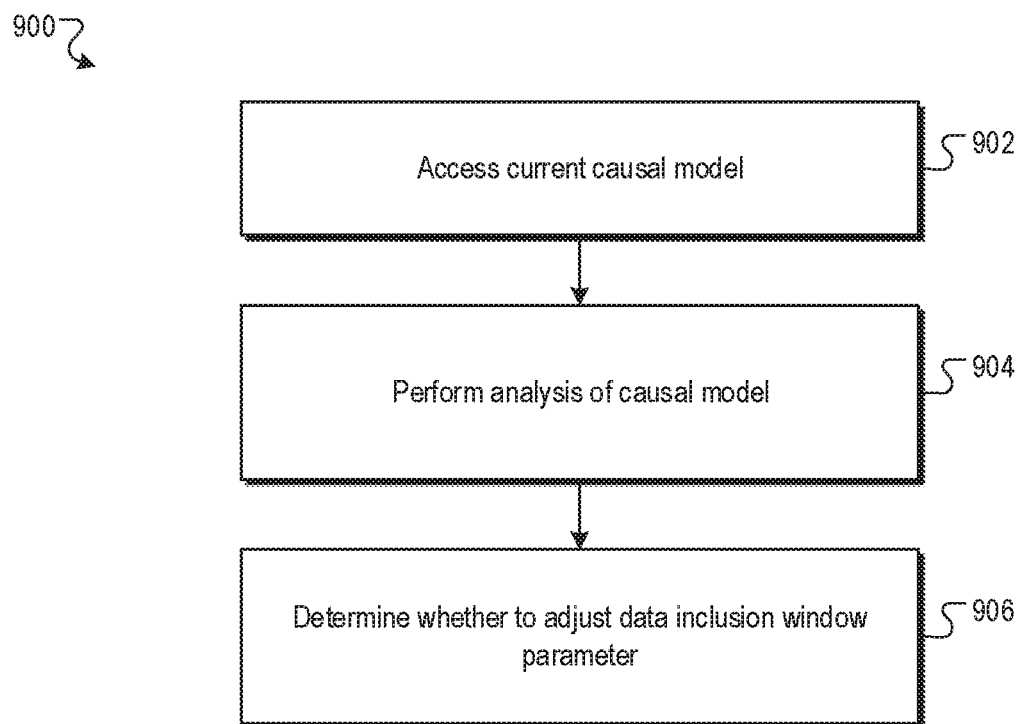
FIG. 9 is a flow diagram of an example process for updating the value of a data inclusion value for a given controllable element based on heuristics.

FIG. 9 is a flow diagram of an example process 900 for updating the value of a data inclusion value for a given controllable element based on heuristics. For convenience, the process 900 will be described as being performed by a system of one or more computers located in one or more locations. For example, a control system, e.g., the control system 100 of FIG. 1, appropriately programmed, can perform the process 900.

Generally, the system performs the process 900 for the data inclusion window when the data inclusion window is a parameter that is being varied based on heuristics and not using stochastic variation.

When the system maintains multiple clusters for the given controllable element, the system can perform the process 900 independently for each cluster, i.e., so that the data inclusion window for the given controllable element within one cluster can be updated differently from the set of internal parameters for the given controllable element within another cluster.

The system accesses the current causal model for the given controllable element (step 902).

The system analyzes one or more properties of the current causal model (step 904). For example, the system can perform a normality test to determine whether the d-scores for the various possible control settings for the given controllable element are normally distributed (step 904). In particular, the system can conduct a normality test, e.g., a Shapiro-Wilk test, on the d-score distributions for the given controllable element in the current causal model. Generally, the system scales and pools together the d-score distributions between the different possible settings to generate a single distribution and then performs the normality test on the single distribution. The system can perform this test for different data inclusion windows, e.g., for the current causal model computed using the current data inclusion window and one or more alternative causal models computed using one or more alternative data inclusion windows, to find the longest data inclusion window that satisfies the normality test with some prescribed p-value.

As another particular example, the system can measure the overlap in the confidence intervals between different impact measurements in the given controllable element in the current causal model. The system can perform this test for different data inclusion windows, e.g., for the current causal model computed using the current data inclusion window and one or more alternative causal models computed using one or more alternative data inclusion windows, to find the data inclusion window that comes closest to a desired degree of overlap.

As another particular example, the system can compute a statistical power analysis to identify the sample size that will result in the current causal model having a desired statistical power. The system can then adjust the data inclusion window so the number of instances included in the adjusted window equals the identified sample size.

The system determines whether to adjust the data inclusion window parameter based on the results of the analysis (step 906). For example, the system can adjust the data inclusion window parameter to specify the longest data inclusion window that satisfies the normality test as described above, or to the data inclusion window that comes closest to the desired degree of overlap, or to the data inclusion window that includes the number of instances that equals the identified sample size.

The example of FIG. 9 is an example of adjusting the data inclusion window based on a heuristic. However, in general, any of the internal parameters can be adjusted based on a heuristic (instead of held fixed or adjusted using stochastic variation). A few examples of setting internal parameters based on heuristics follow.

As one example, the system can set the value of the ratio parameter using a statistical power analysis. In particular, the system can perform a statistical power analysis to compute the minimum number of baseline instances that are required to determine that the hybrid instances outperform the baseline instances with a threshold statistic power. The system can then adjust the value of the ratio parameter to be equal to this minimum number.

As another example, to set the value of the cluster size hyperparameter, the system can perform an a priori statistical power analysis to determine a sufficient amount of environment responses that are required in order for the causal model to have a desired statistical power, i.e., instead of a range as described above, and set the value for the cluster size to this range.

The above description describes how the system can modify internal parameters during operation of the system. This adjustment of internal parameters can allow the system to effectively account for changes in the properties of the environment, i.e., for environments where the mapping from control settings to environment responses is not static and can change at various times during the operation of the system. Unless properly accounted for, changes in the properties of the environment that do not equally impact all possible control settings for all controllable elements can result in inaccurate causal models that are based on stale data that is no longer relevant and therefore can decrease the effectiveness of the system in controlling the environment.

Figure 10:
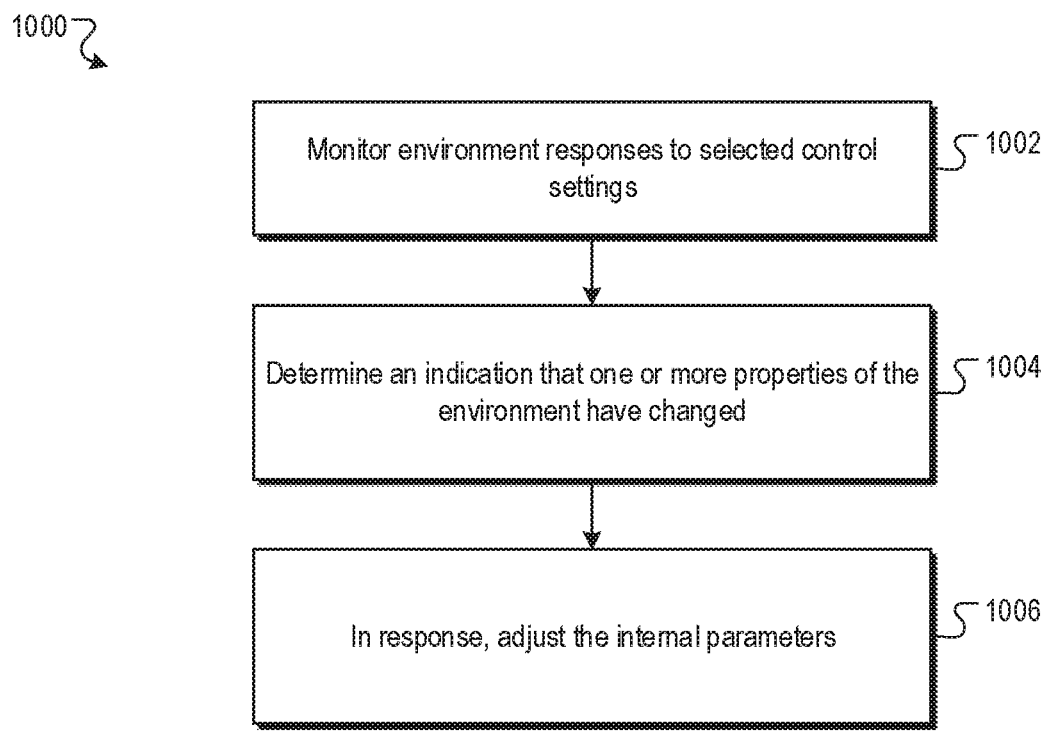
FIG. 10 is a flow diagram of an example process for responding to a change in one or more properties of the environment.

FIG. 10 is a flow diagram of an example process 1000 for responding to a change in one or more properties of the environment. For convenience, the process 1000 will be described as being performed by a system of one or more computers located in one or more locations. For example, a control system, e.g., the control system 100 of FIG. 1, appropriately programmed, can perform the process 1000.

The system monitors environment responses to control settings selected by the system (step 1002). That is, as described above, the system repeatedly selects control settings and monitors responses to those selected control settings.

The system determines an indication that one or more properties of the environment have changed (step 1004). In particular, the change in the properties of the environment is one that modifies the relative impact that different settings for at least one of the controllable elements have on the environment responses that are being monitored by the system. That is, by determining an indication that one or more properties have changed, the system determines that it is likely that the relative causal effects of different settings on the environment responses have changed, i.e., as opposed to a global change that affects all of the possible control settings differently. While the system does not have access to direct information specifying that a change has occurred, the system can determine based on the monitored environment responses an indication that the change has likely occurred.

For example, the system can determine an indication that a change has occurred when the difference between the current system performance and the baseline system performance is decreasing. In particular, as described in more detail below, the system can determine this based on the performance metric increasing for smaller possible values of the data inclusion window, i.e., as reflected by the causal model for the data inclusion window described above.

As another example, the system can determine an indication that a change has occurred when, as described above, a normality test determines that the d-scores for the possible settings of the controllable element are no longer normally distributed.

In response to determining the indication that one or more properties of the environment have changed, the system adjusts the internal parameters of the system (step 1006).

Generally, the system adjusts the values of the internal parameters to indicate that there is an increased level of uncertainty about whether the causal model maintained by the system accurately captures the causal relationships between control settings and environment responses.

For example, the system can adjust the data inclusion window parameters to shrink the data inclusion window, i.e., so that only more recent historical environment responses will be included when determining the causal model. That is, the system can adjust the data inclusion window parameters so that the range of possible data inclusion windows favors shorter data inclusion windows.

As another example, the system can adjust the ratio parameters to decrease the hybrid-to-explore ratio, i.e., so that there are fewer hybrid instances relative to explore instances. By decreasing the ratio, the system places less reliance on the current causal model when selecting control settings and instead more frequently explores the space of possible control settings. That is, the system can adjust the ratio parameters so that the range of possible ratios favors smaller ratios.

As another example, the system can adjust the clustering parameters to decrease the number of clusters that the instances are clustered into. By decreasing the number of clusters, the system prevents the causal model from clustering on characteristics that may no longer be relevant when explaining differences in system performance between clusters.

Figure 11:
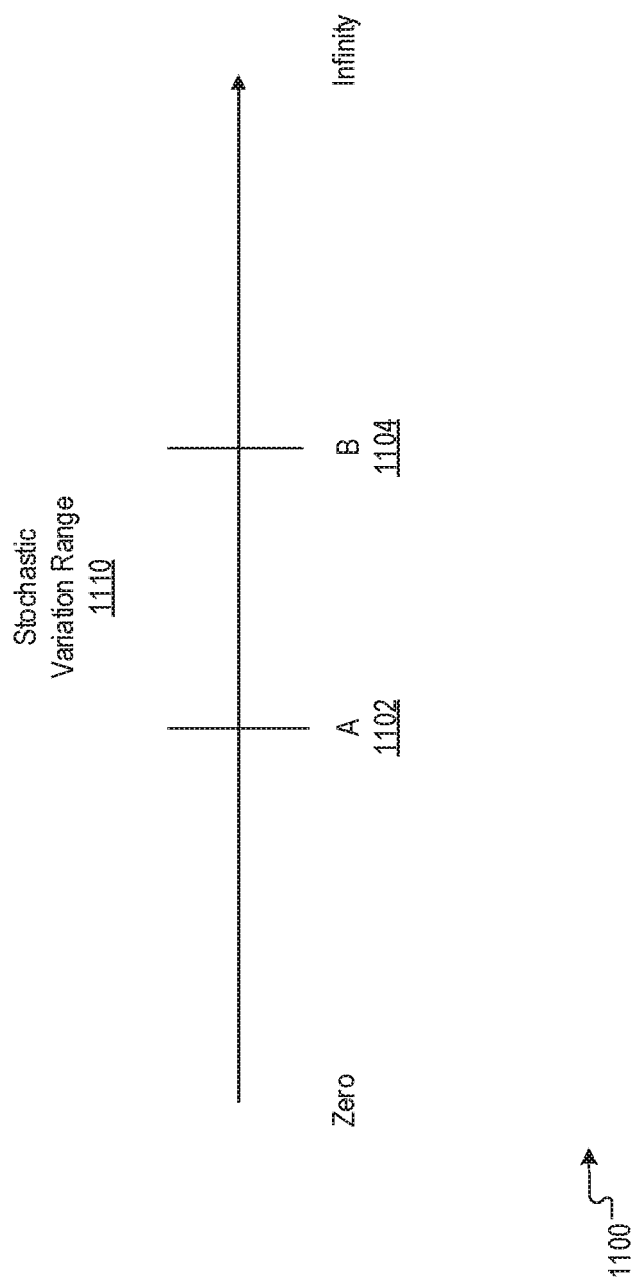
FIG. 11 shows a representation of the data inclusion window for a given controllable element of the environment when the set of internal parameters that define the data inclusion are stochastically varied.

FIG. 11 shows a representation 1100 of the data inclusion window for a given controllable element of the environment when the set of internal parameters that define the data inclusion are stochastically varied. As can be seen in the example of FIG. 11, while the data inclusion window could range from zero (i.e., no data is included) to infinity (i.e., all procedural instances are included), the current stochastic variation range 110 from which data inclusion windows for the given controllable element are sampled is between a lower bound A 1102 and an upper bound B 1104. In some cases, the lower bound A 1102 and the upper bound B 1104 are fixed and the system adjusts the probabilities that are assigned to different values between the lower bound A 1102 and the upper bound B 1104 by updating the causal model as described above. In other cases, the system can vary the lower bound A 1102 and the upper bound B 1104 while also updating the causal model. In particular, the system can adjust the range 1110 based on the likelihood that relative causal effects of different possible values of the controllable element are changing.

In particular, as shown in FIG. 11, the system maintains a range of possible values for the data inclusion window. That is, the data inclusion window parameters include the lower bound of the range, the upper bound of the range, and the possible values that the data inclusion window can take within the range. The data inclusion window parameters also include probabilities for the possible values that are used when stochastically sampling values. As described above with reference to FIG. 8, these probabilities are adjusted by the system In some cases, the range of possible values is fixed. In other cases, however, the system varies the lower and upper bounds of the range based on one or more heuristics to adjust the possible data inclusion windows that are explored by the system and to prevent the system from exploring data inclusion windows that too short or too long.

For example, the system can compute a statistical power curve that represents the impact that changes in sample size (via changes in data inclusion window) will have on the width of the confidence intervals the current causal model is using for the controllable element. Given the nature of statistical power curves, the confidence intervals become more precise quickly at the small end of the sample size but, as the sample size increases, each additional increase in sample size results in a disproportionately smaller increase in the precision of the confidence intervals (i.e., disproportionally smaller decrease in the width of the confidence intervals). Thus, exploring longer data inclusion windows may lead to very little gain in statistical power and comes with a high risk of not accurately representing the current decision space. To account for this, the system can then constrain the range of the data inclusion window to result in a number of samples that falls between a lower threshold and an upper threshold on the statistical power curve. By constraining the data inclusion window in this way, the system does not explore data inclusion windows that so short as to result in too little statistical power to compute significant confidence intervals, i.e., does not explore data inclusion windows that result in insufficient data to compute statistically significant confidence intervals. The system also does not explore data inclusion windows that are unnecessarily long, i.e., that data inclusion windows that result in small gains in statistical power in exchange for the risk of failing to account for recent changes in the properties of the environment.

As another example, the system can compute a stability measure, e.g., a factorial analysis, of the interaction between time and the relative impact measurements of the possible control settings for the controllable element. That is, the system can determine the stability of the causal relationships over time. The system can increase either the upper bound or both the upper bound and the lower bound of the data inclusion window range when the stability measure indicates that causal relationships are stable while decreasing the upper bound or both the upper bound and lower bound when the stability measure indicates that the causal relationships are unstable, i.e., dynamically changing. This allows the system to explore smaller data inclusion windows and disregard older data when there is higher probability that the properties of the environment are changing while exploring larger data inclusion windows when there is a higher probability that the properties of the environment are stable.

As yet another example, the system can adjust the range based on the shape of the causal model as described above. In particular, the system can explore a range of longer data inclusion windows when the impact measurements are growing in magnitude as data inclusion window gets higher and a range of smaller data inclusion windows when the impact measurements are growing in magnitude as data inclusion window gets shorter. In other words, the system can move the range down when the difference decreases while moving the range up when the difference increases. This allows the system to explore smaller data inclusion windows and disregard older data when there is higher probability that the properties of the environment are changing.

In some cases, the system can apply some combination of these heuristics, e.g., by allowing the upper bound to increase based on either or both of the latter two examples so long as the upper bound does not exceed the size that corresponds to the upper threshold on the statistical power curve and by allowing the lower bound to decrease based on either or both of the latter two examples so long as the lower bound does not fall below the size that corresponds to the lower threshold on the statistical power curve.

While these examples are described with respect to the data inclusion window, similar heuristics can also be used to adjust the ratio of hybrid to baseline instances, i.e., to increase the number of baseline instances when the probability that the properties of the environment are changing or have recently changed are higher and to decrease the number of baseline instances when the probability that the properties of the environment is stable is higher.

Figure 12:
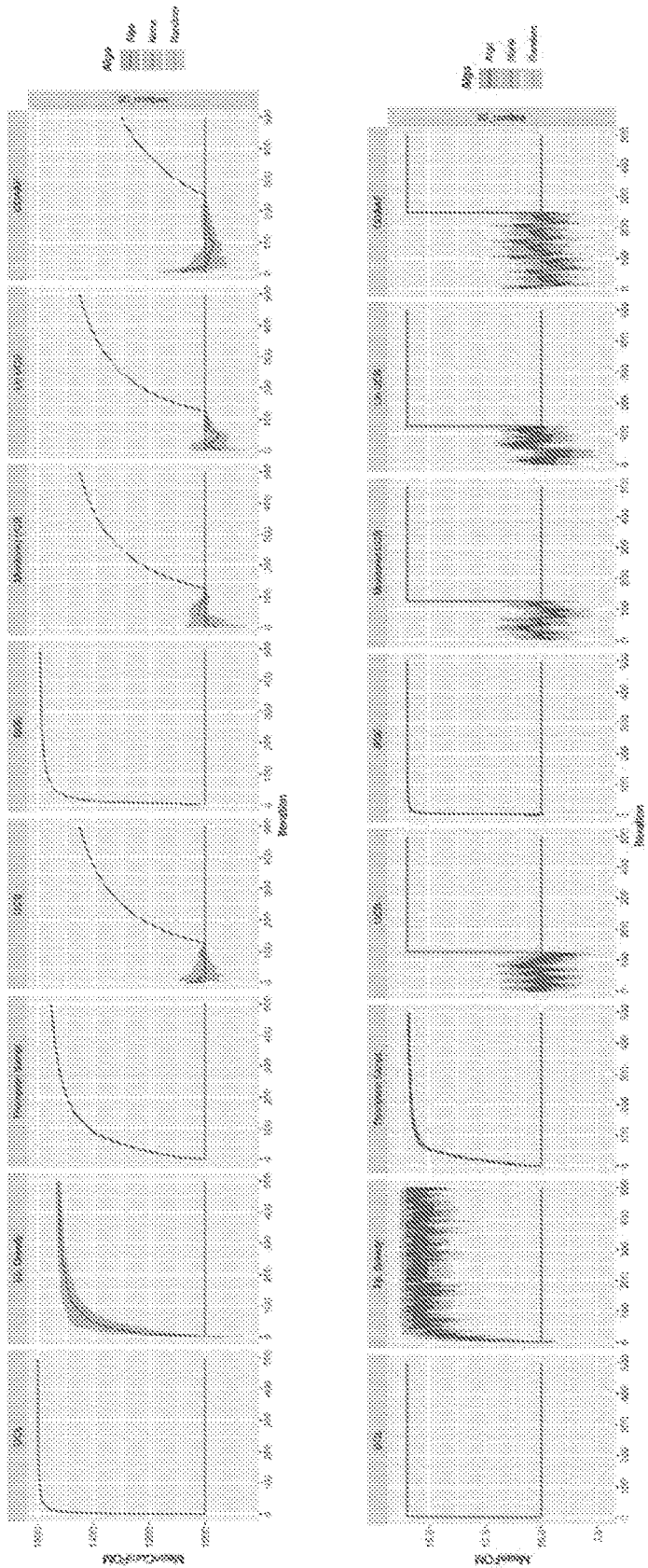
FIG. 12 shows the performance of the described system when controlling an environment relative to the performance of systems that control the same environment using existing control schemes.

FIG. 12 shows the performance of the described system (denoted as "DCL" in FIGS. 12-18) when controlling an environment relative to the performance of systems that control the same environment using existing control schemes. In particular, FIG. 12 shows the performance of the described system compared to three different kinds of existing control schemes: (i) a "none" scheme in which a system does not select any settings and receives only the baseline environment responses (ii) a "random" scheme in which a system assigns control settings randomly without replacement, and (iii) various state-of-the-art reinforcement learning algorithms.

In the example of FIG. 12, the environment that is being controlled has 3 controllable elements each with 5 possible control settings and the value of the performance metric at each iteration is drawn from a Gaussian distribution which is fixed throughout. Application of particular control settings changes the parameters of the Gaussian distribution from which the value of the performance metric is drawn. These characteristics are similar to those found in simple or highly-controlled real-world environments, for example certain manufacturing lines, but lack the additional complexities that can be encountered in more complex real-world environments.

The upper set of plots in FIG. 12 shows the performance of each system in terms of mean cumulative FOM ("Mean-CumFOM"). The mean cumulative FOM at any given iteration is the average value of the performance metrics, i.e., FOM, received starting from the first iteration and through the given iteration, i.e., the cumulative average performance metric value across time.

The lower set of plots in FIG. 12 shows performance of each system by mean FOM per instance ("MeanFOM") The mean FOM per instance at any given iteration is the mean of the performance metrics received for the instance at the given iteration, i.e., without considering earlier iterations.

Generally, the first column ("DCL") shows the results for the described system while the remaining columns show results for the existing control schemes.

As indicated above, the environment for which the results are shown in FIG. 12 is less complex than many real-world environments, e.g., because the causal effects are fixed, there are no external uncontrollable characteristics that impact the performance measures and there is no uncertainty about the spatial or temporal extent. However, even in this relatively simple environment the performance of the described system meets or exceeds the performance of state-of-the-art systems, with or without the advanced features enabled.

A description of the state-of-the-art systems that are used to benchmark the performance of the system follows:

BGE—Boltzmann-Gumbel Exploration [Cesa-Bianchi et al. Boltzmann Exploration Done Right, Conference on Neural Information Processing Systems (NeurIPS), 2017] is a multi-armed bandit algorithm which uses an exponential weighting approach for control setting assignment selection. It maintains a distribution over FOMs for each control setting assignment. At each step, a sample is generated from each of these distributions and the control setting assignment corresponding to the largest sample is selected by the algorithm. The internal parameters of the distributions are then updated using the received feedback.

Ep Greedy—Epsilon Greedy is a general-purpose multi-armed bandit algorithm that selects a random control setting assignment with probability epsilon and selects the control setting assignment which has given highest average FOM in the past with probability 1-epsilon. In effect, it explores epsilon percent of the time and exploits 1-epsilon percent of the time.

UCB—The Upper Confidence Bound (UCB) [Auer et al. Finite-time Analysis of the Multiarmed Bandit Problem, Machine Learning, 2002] multi-armed bandit algorithm is one of two fundamental approaches to solving multi-armed bandit problems. It works by computing the average FOM and confidence interval from historical data. It selects a control setting assignment by computing the control setting assignment with highest average FOM plus confidence interval. In this way it acts optimistically about the control setting assignment's potential FOM and learns over time which control setting assignment has the highest FOM.

Lin UCB—LinUCB [Li et al. A Contextual-Bandit Approach to Personalized News Article Recommendation, International World Wide Web Conference (WWW), 2010] builds on UCB by maintaining an average FOM and confidence interval and makes a key assumption that the expected FOM is a linear function of the characteristics of the procedural instances and the control setting assignments in the experiment. The algorithm is then able to select the control setting assignment that is best for any individual procedural instance. Lin UCB is expected to perform best in situations where the ideal control setting assignment is different for different procedural instance groups.

Monitored UCB—Monitored UCB [Cao et al. Nearly Optimal Adaptive Procedure with Change Detection for Piecewise-Stationary Bandit, International Conference on Artificial Intelligence and Statistics (AISTATS), 2019] builds on UCB by computing the average FOM and confidence interval but is designed for environments where abrupt changes in the FOM can occur. As such, it incorporates a change point detection algorithm which identifies when the FOM changes and resets the internal parameters (effectively resetting the average FOM and confidence interval) to start learning the new FOM. Monitored UCB is expected to perform well (better than UCB and variants) in environments where an abrupt change in the FOM occurs.

ODAAF—Optimism for Delayed Aggregated Anonymous Feedback [Pike-Burke et al. Bandits with Delayed, Aggregated Anonymous Feedback, International Conference on Machine Learning (ICML), 2018] is a multi-armed bandit algorithm designed to work in a setting where feedbacks suffer from random bounded delays. Feedbacks are additively aggregated and anonymized before being sent to the algorithm, which makes this setting significantly more challenging. The algorithm proceeds in phases, maintaining a set of candidates for the possible optimal control setting assignments. In each phase, it plays an iterated round robin strategy amongst these candidates and updates their performance metric value estimates as it receives feedbacks. At the end of each phase, the algorithm eliminates the candidates whose estimated performance metric values are significantly suboptimal.

Thompson Sampling—Thompson Sampling [Agrawal and Goyal. Analysis of Thompson Sampling for the Multi-armed Bandit Problem, Conference on Learning Theory (COLT), 2012] is a probability matching algorithm and is the other fundamental approach to solving multi-armed bandit problems (the other being optimism-based approaches like UCB). It works by maintaining a distribution over the estimated FOM for each control setting assignment option, sampling from each distribution, and then selecting the control setting assignment option with highest sampled (estimated) FOM. Once the true FOM is observed, the (posteriori) distributions are updated using a Bayesian approach. The algorithm selects each control setting assignment proportional to its probability of being the best control setting assignment.

Figure 13:
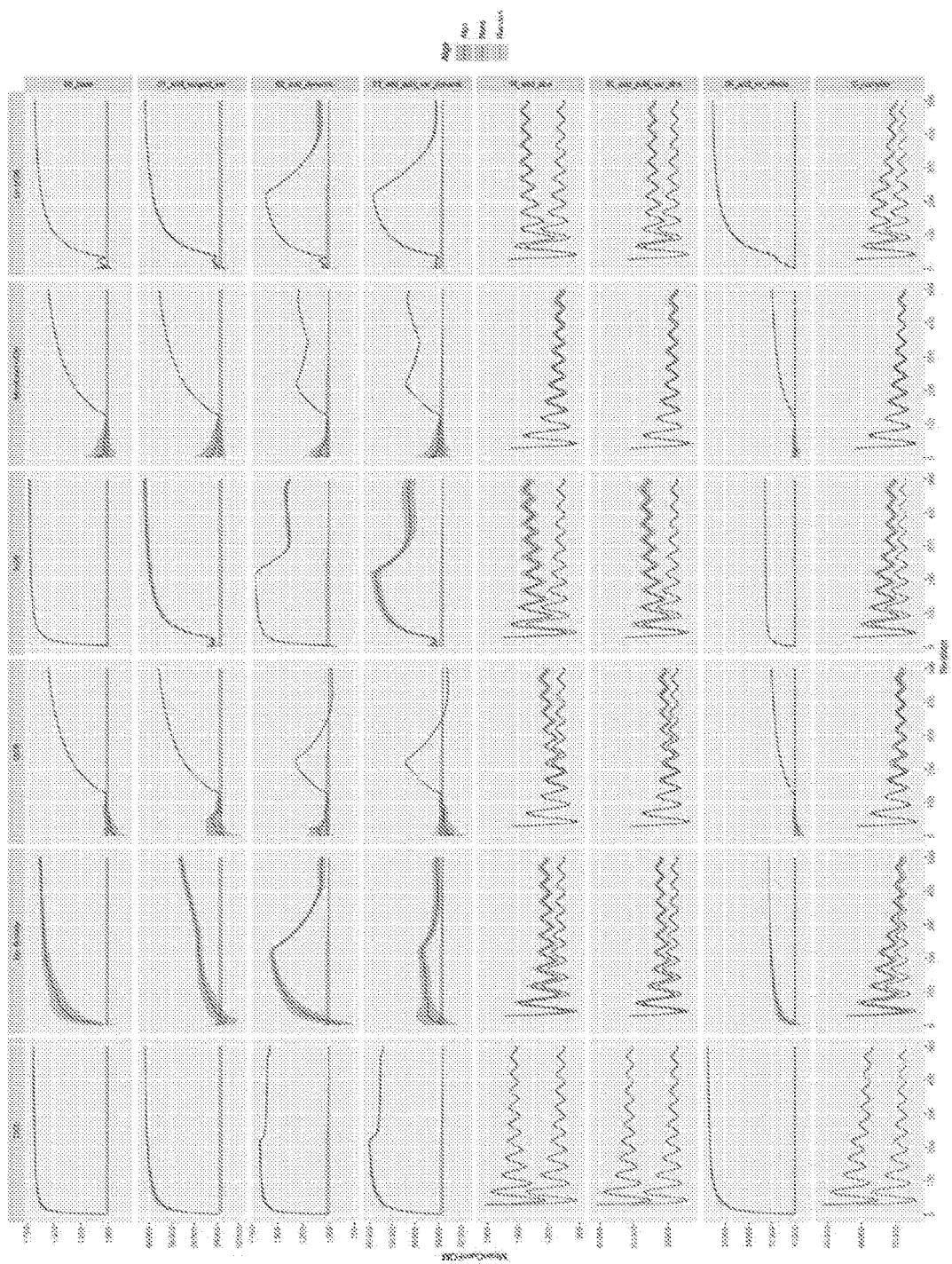
FIG. 13 shows the performance of the described system relative to the performance of multiple other systems when controlling multiple different environments.

FIG. 13 shows the performance of the described system relative to the performance of multiple other systems when controlling multiple different environments.

In particular, each of the other systems uses a respective one of the existing control schemes described above to control multiple different environments.

The environments that are being controlled each have 3 controllable elements each with 5 possible settings and the values of the performance metric being optimized at each iteration are drawn from a Gaussian distribution.

The environments have varied complexity through the addition of various factors that cause variability between different procedural instances.

In particular, the base environment shown in the top set of graphs changes the mean and variance of the Gaussian distribution depending on the procedural instance, i.e., so that different procedural instances can receive different performance metric values even if the same control settings are selected.

Others of the environments also introduce time-based changes in the effects of applying different possible settings for the controllable elements, underlying sinusoidal behavior in the performance metric, and different setting effects for different instance groups, i.e., that represent interactions between environment characteristics and controllable elements.

As can be seen from FIG. 13, many of the existing control schemes generally do well in the simple, baseline case and a given control scheme might do well with one additional complexity factor, but none of the existing control schemes perform well in all cases. The described system, on the other hand, performs comparably to or better than the best existing control scheme in all of the environments. Thus, the example of FIG. 13 shows that the described system is able to perform at similar or better possible settings than the other control schemes for each of the different environments because of the ability of the system to automatically adapt to varied, complex environments without requiring manual model selection, i.e., by continually varying the internal parameters of the system to account for different properties of different environments even when no prior knowledge of the properties of the environment was available.

A detailed explanation of each of the environments being controlled follows.

- 00_base—100 procedural instances; 3 controllable elements with 5 possible settings each with the performance metric value drawn from a Gaussian distribution. Selection of different IV Possible settings changes the mean and/or standard deviation of the distribution. This environment is relatively simple but does have many combinations of possible control settings as is often found in real-world environments.
- 01_add_subject_var—starting from 00_base, the procedural instances are divided into 3 groups with different base-rate means and standard deviations for their performance metric value distributions. This introduces additional variance in the data without changing the effects of control setting assignments. procedural instance/EU variance of this type is very typical of the real world. For example, this specific configuration mimics sales behavior of an assortment of products where a small group of products account for a bulk of overall sales (a la 80/20 rule), a larger group of products have middling sales, and most products have low sales.
- 02_add_dynamic—starting from 00_base, the effects of the IV Possible settings undergo multiple transitions at predetermined times (unknown to the algorithms) such that the impact of IV Possible settings is reversed. This changing behavior is very typical of the real world. For example, effectiveness of different advertising campaigns and techniques regularly changes over space and time (what worked before isn't likely to work now). Similarly, optimal control setting assignment choices on a manufacturing line will vary due to factors like temperature, humidity, and the nuances of specific equipment, e.g., wear and tear.
- 03_add_subject_var_dynamic—a combination of 01_add_subject_var and 02_add_dynamic. The combination of these two behaviors (described above) make this environment even more similar to many dynamic real-world environments.
- 04_add_sine—starting from 00 base, adds an overall sinusoidal pattern to the performance metric values. This simulates periodic trends (e.g. seasonal, weekly) in the FOM that are independent of the effects of the IV Possible settings. Some algorithms have difficulty dealing with the additional data variance. Periodic behavior of this type is very typical of the real world. For example, retail sales, supply chains, and so on, often follow weekly, monthly, and seasonal cycles that introduce significant variance in performance metrics. As another example, manufacturing and other processes that are impacted by seasonal changes in weather may also experience similar effects. A key challenge in these situations (that the described system addresses) is to be able to differentiate the impact of marketing activities (for example) from these underlying behaviors.
- 05_add_subject_var_sine—a combination of 01_add_subject_var and 04_add_sine. The combination of these two behaviors (described above) make this environment even more similar to complex and dynamic real-world environments.
- 06_add_ev_effects—the optimal combination of IV Possible settings is different for some procedural instances. This variation in control setting assignment is very typical of real-world situations. For example, different advertising or promotional approaches will work better than others depending on the products involved, recipients of content, space, time, etc.
- 10_complex—a combination of 01_add_subject_var, 02_add_dynamic, 04_add_sine, and 06_add_ev_effects. This environment does the most to capture the behaviors of the real world in that it takes all of the above described real-world behaviors and combines them into one environment.

Figure 14:
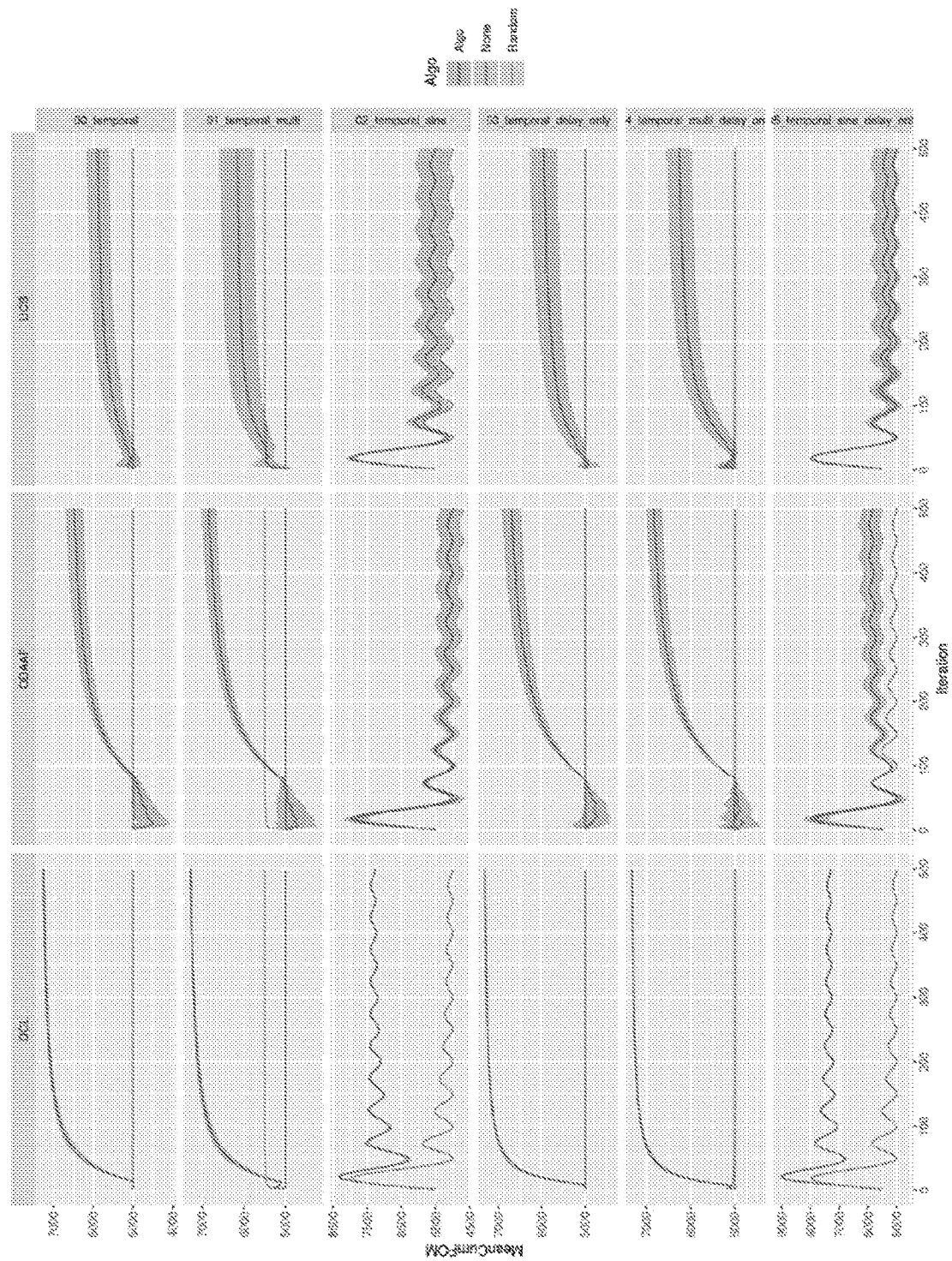
FIG. 14 shows the performance of the described system relative to the performance of multiple other systems when controlling multiple different environments that have varied temporal effects.

FIG. 14 shows the performance of the described system relative to the performance of multiple other systems when controlling multiple different environments that have varied temporal effects.

In particular, each of the other systems uses a corresponding existing control scheme to control multiple different environments.

The environments that are being controlled have 4 controllable elements each with 2 possible settings and the performance metric values at each iteration are drawn from a Gaussian distribution. The environments have varied temporal delays and durations imposed that affect when the performance metric values are produced relative to initial application of control settings for a given instance. For example, in the top environment, the environment responses for all effects are delayed by 2 time iterations and last for 3 time iterations. In the following environment, the 4 controllable elements all have different temporal delays and durations. The third and fourth environments add additional complexity and variability.

As can be seen from the example of FIG. 14, the described system is able to perform at similar or better possible settings than the other control schemes for each of the different environments. This showcases the described system's ability to dynamically adapt to the temporal behavior of the effects of applying control settings, i.e., by varying the temporal extent parameters during operation.

In addition, two of the environments include underlying periodic behavior unrelated to IV control setting assignment effects. This behavior is typical of situations encountered in the real world (e.g. advertising, pharmaceuticals) where actions taken have a delayed rather than immediate effect. At the same time, such scenarios often have a residual effect that lasts after control setting assignment is discontinued. In addition, it would be rare to find these temporal behaviors in isolation. Rather, they will most often co-occur with underlying behaviors similar do the sinusoidal pattern shown. As can be seen from FIG. 14, the described system outperforms the conventional systems, i.e., due to being better able to account for different temporal behaviors by adjusting the temporal extent parameters and other internal parameters to adjust to changes in underlying behaviors.

Details of the environments shown in FIG. 14 follow.

- 00_temporal—500 procedural instances; 4 controllable elements with 2 possible settings each with the performance metric value drawn from a Gaussian distribution. Selection of different IV Possible settings changes the mean and/or standard deviation of the distribution. Performance metric values for all effects are delayed by 2 time iterations and last 3 iterations.

01_temporal_multi—same as 00_temporal except that the 4 controllable elements have different temporal delays and durations.

02_temporal_sine—starting from 00_base with sinusoidal behavior added

03_temporal_delay_only—same as 00_temporal but with durational behavior removed

Figure 15:
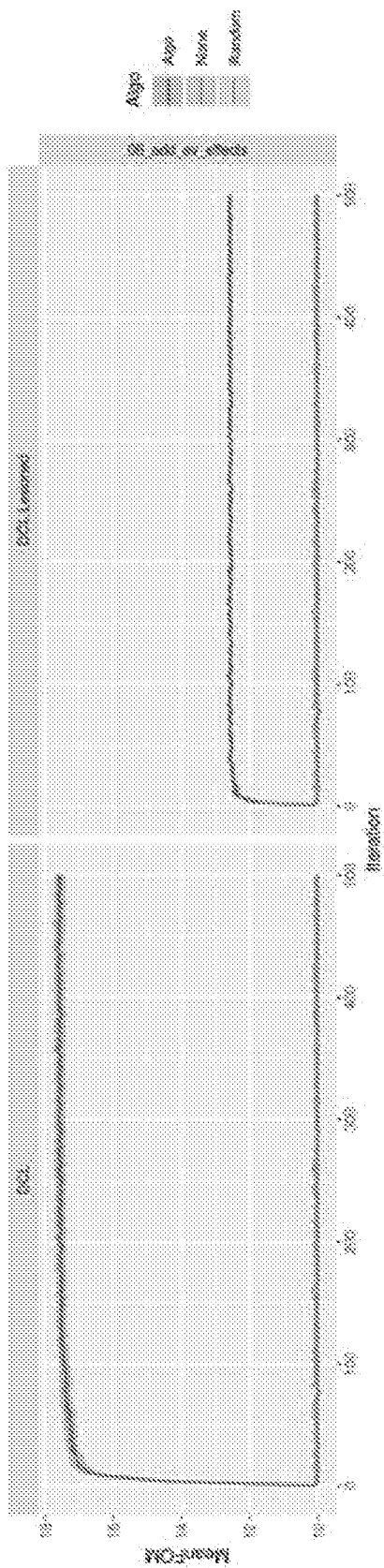
FIG. 15 shows the performance of the described system with and without clustering.

04_temporal_multi_delay_only—same as 01_temporal_multi but with durational behavior removed 05_temporal_sine_delay_only—same as 02_temporal_sine but with durational behavior removed FIG. 15 shows the performance of the described system with and without Clustering. The environment that is being controlled has 3 controllable elements each with 5 possible settings and the performance metric value at each iteration is drawn from a Gaussian distribution which is fixed throughout the experiment. The environment being controlled has different optimal control setting assignments (controllable elements) depending on the characteristics of the procedural instances/EUs described by the Environment characteristics. One set of control setting assignments will produce good results overall but in fact be negative for a sub-population. If the sub-population is given its specific ideal control setting assignment, the overall utility is improved. This is typical of real-world situations where optimal control setting assignment may vary greatly based on external characteristics. The left figure shows the performance of the described system with the clustering component included. In this case, the described system assigns specific control setting assignment for procedural instances/EUs, which results in overall higher FOM. The right figure shows the performance of the described system without using the clustering component, i.e., without ever entering the clustering phase. In this case, the algorithm utilizes a single overall control setting assignment approach for all procedural instances, which causes it to use a non-optimal control setting assignment for a certain sub-population. As can be seen from FIG. 15, the described system performs better when clustering is used.

Figure 16:
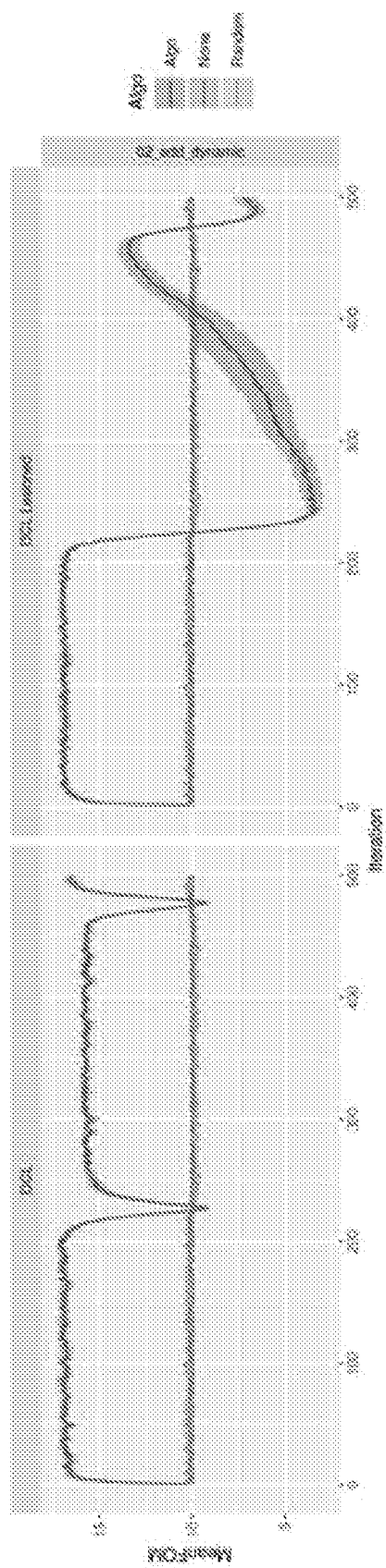
FIG. 16 shows the performance of the described system with the ability to vary the data inclusion relative to the performance of the described system controlling the same environment while holding the data inclusion window parameters fixed.

FIG. 16 shows the performance of the described system with the ability to vary the data inclusion relative to the performance of the described system controlling the same environment while holding the data inclusion window parameters fixed. In the example of FIG. 16, the environment that is being controlled exhibits two gradual changes in the relative effects of control settings on performance measures. This is typical of the real world in two ways 1) the impact of actions (e.g. advertising, manufacturing parameters) is rarely if ever static, 2) when such changes happen, they are often gradual in nature, not abrupt. The left figure shows the performance of the described system with the DIW component included. In this case, the described system is able to rapidly detect, e.g., through hybrid-baseline comparisons, that the effects have changed, and the described system can immediately re-learn the best control setting assignment by shrinking the data inclusion window. The right figure shows the performance of the described system without using the DIW component. In this case, the algorithm adapts to the change in treat effects very gradually. By the time it does so, the effects are already changing again.

Figure 17:
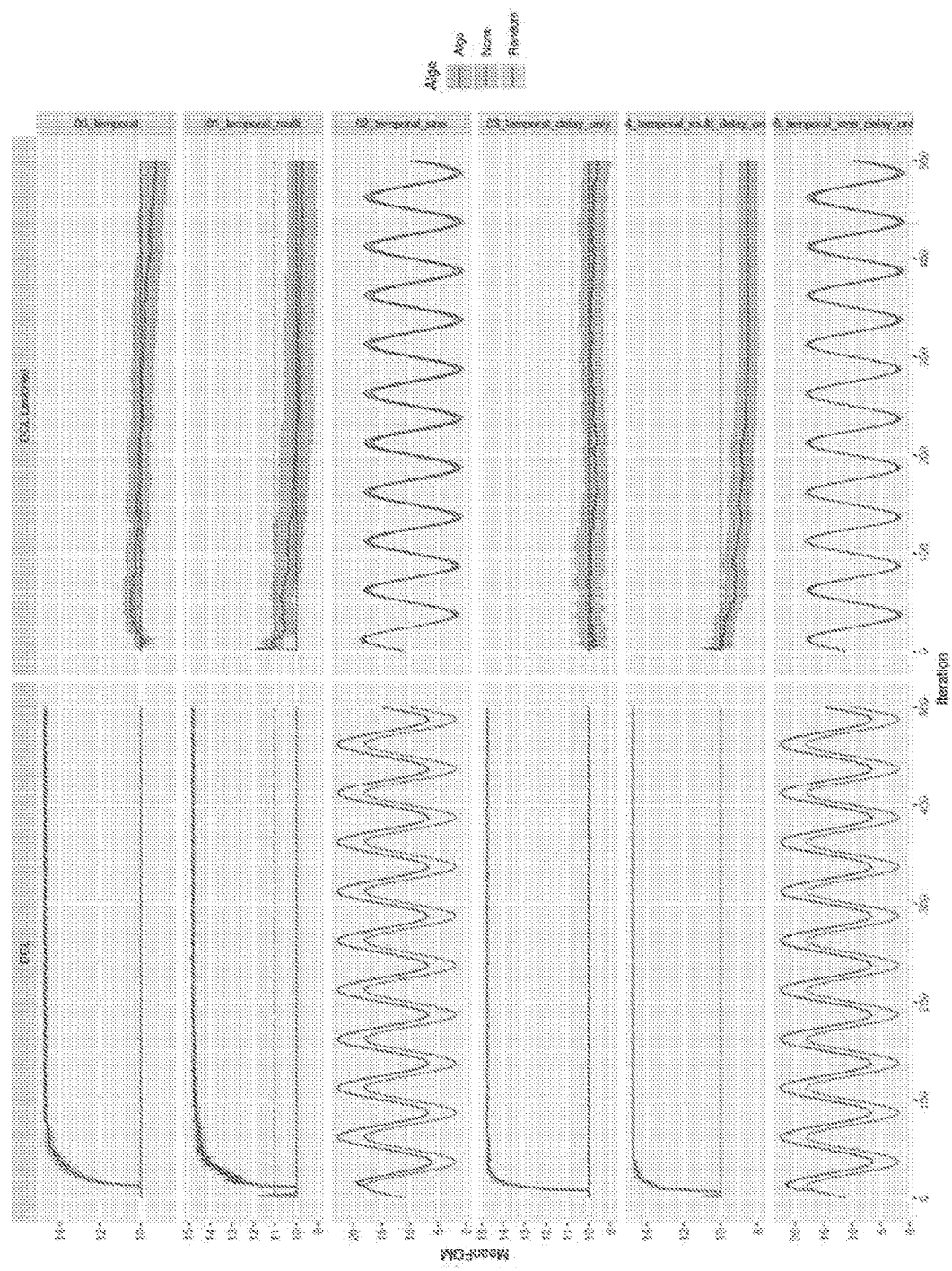
FIG. 17 shows the performance of the described system with and without temporal analysis, i.e., with the ability to vary the temporal extent and without.

FIG. 17 shows the performance of the described system with and without Temporal analysis, i.e., with the ability to vary the temporal extent and without. The environment that is being controlled has 4 controllable elements each with 2 possible settings and the performance metric value at each iteration is drawn from a Gaussian distribution which is fixed throughout the experiment. The environments have varied temporal delays and carryover behavior imposed that affect when the performance metric values are produced relative to initial application of IV possible settings. In addition, two of the environments include underlying periodic behavior unrelated to effect. This behavior is typical of situations encountered in the real world (e.g. advertising, pharmaceuticals) in that very often actions taken do not have an immediate effect and they often have a residual effect even after control setting assignment is discontinued. And in addition, this temporal variation is often present in the context of other underlying behavior. This figure illustrates the value of the temporal optimization within the described system. The left column shows the performance of the described system using the temporal component. The right column shows the performance of the described system without using the temporal component. As can be seen from the example of FIG. 17, the described system performs significantly better when temporal analysis is used when the environment has these temporal properties.

Figure 18:
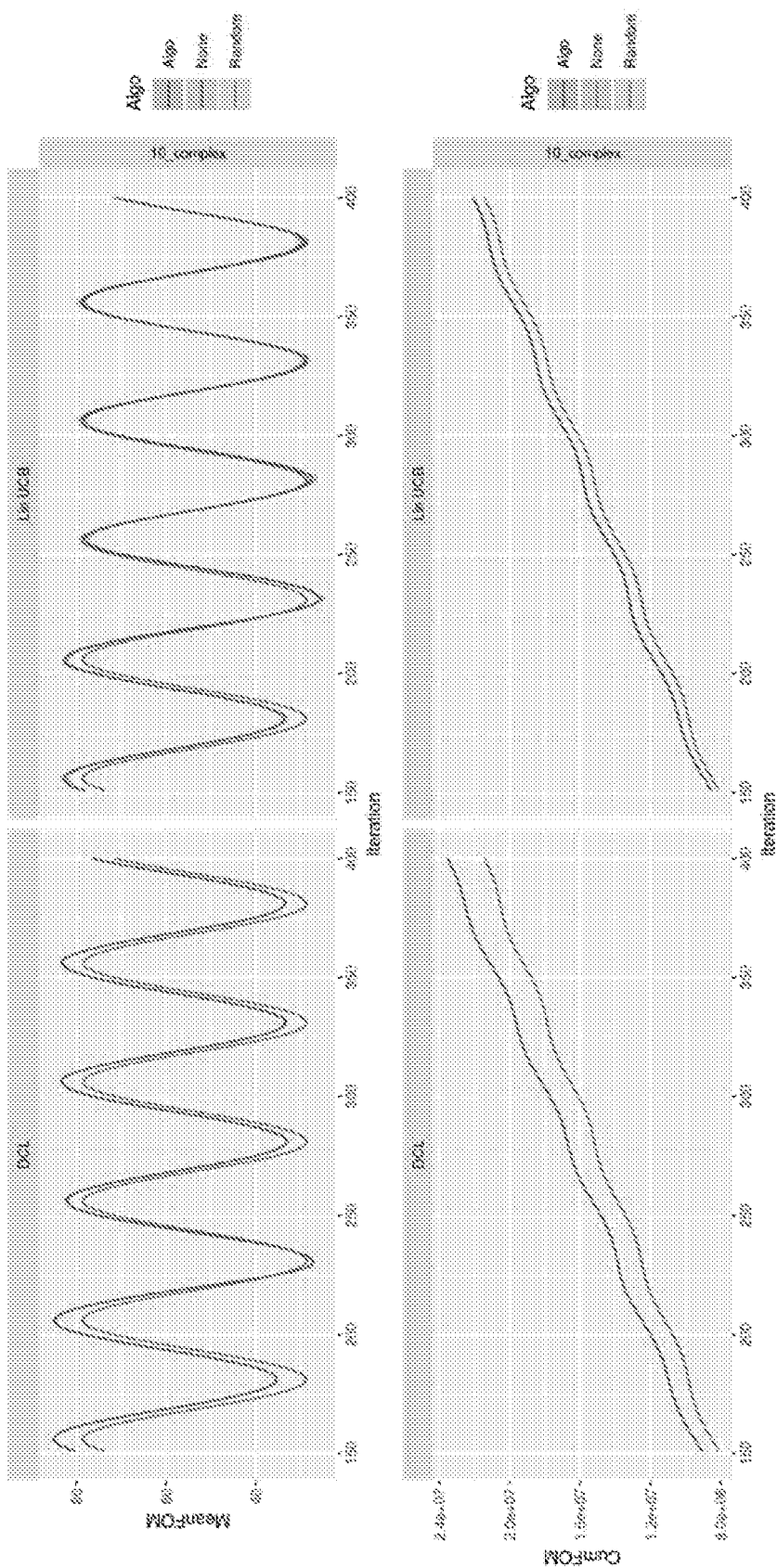
FIG. 18 shows the performance of the described system when controlling an environment relative to the performance of a system that controls the same environment using an existing control scheme ("ucb_lin").

FIG. 18 shows the performance of the described system when controlling an environment relative to the performance of a system that controls the same environment using an existing control scheme ("Lin UCB"). In the example of FIG. 18, the environment that is being controlled has cyclic underlying behavior unrelated to IV possible setting effects along with changes in these effects such that the optimal control setting assignment changes over time. These characteristics are similar to those found in many real-world environments, where there are regular underlying dynamics (e.g. weekly, monthly, or seasonal patterns) along with changes over time in the impact of control setting assignments/actions. FIG. 18 shows a subset of time during which, the impacts of IV possible settings are changing in the underlying environment (during iterations 200-250). As can be seen from FIG. 18, the performance of the existing control scheme stays in exploit phase based on the previous control setting assignment effects and is unable to rapidly adapt to the change. On the other hand, the performance of the described system adapts to the changing effects quickly and finds incremental improvements under the altered environment effects (upper plots). This results in an increased incremental benefit from the described system (lower plots). Notice that as time continues, the cumulative benefit of utilizing the described system will continue to increase.

While the above description uses certain terms to refer to features of the described system or actions performed by the described system, it should be understood that these are not the only terms that can be used to describe the operation of the system. Some examples of alternative terminology follow. As one example, the controllable elements may instead be referred to as independent variables (IVs). As another example, the environment characteristics may instead be referred to as external variables (EVs). As another example, the environment responses may instead be referred to as dependent variable (DVs). As another example, procedural instances may instead be referred to as experimental units or self-organized experimental units (SOEUs). As another example, the possible settings for a controllable element may instead be referred to as levels of the element (or of the IV). As yet another example, control settings may instead be referred to as process decisions and assigning control settings for a procedural instance may be referred to as treatment assignment.

The term "repeatedly," i.e., in the context of repeatedly performing an operation is generally used in this specification to mean that the operation is occurring multiple times with or without a specific sequence. As an example, a process may constantly or iteratively follow a set of steps in a specified order or the steps may be followed randomly or non-sequentially. Additionally, steps may not all be executed with the same frequency, for example treatment assignment may be executed more frequently than updating the causal learning, and the frequency of the latter may change over time, for example as exploit phase becomes dominant and/or as computing capacity/speed requirements change over time.

This specification uses the term "configured" in connection with systems and computer program components. For a system of one or more computers to be configured to perform particular operations or actions means that the system has installed on it software, firmware, hardware, or a combination of them that in operation cause the system to perform the operations or actions. For one or more computer programs to be configured to perform particular operations or actions means that the one or more programs include instructions that, when executed by data processing apparatus, cause the apparatus to perform the operations or actions.

Embodiments of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs. The one or more computer programs can comprise one or more modules of computer program instructions encoded on a tangible non transitory storage medium for execution by, or to control the operation of, data processing apparatus. The computer storage medium can be a machine-readable storage device, a machine-readable storage substrate, a random or serial access memory device, or a combination of one or more of them. Alternatively or in addition, the program instructions can be encoded on an artificially generated propagated signal, e.g., a machine-generated electrical, optical, or electromagnetic signal, that is generated to encode information for transmission to suitable receiver apparatus for execution by a data processing apparatus.

The term "data processing apparatus" refers to data processing hardware and encompasses all kinds of apparatus, devices, and machines for processing data, including by way of example a programmable processor, a computer, or multiple processors or computers. The apparatus can also be, or further include, special purpose logic circuitry, e.g., an FPGA (field programmable gate array) or an ASIC (application specific integrated circuit). The apparatus can optionally include, in addition to hardware, code that creates an execution environment for computer programs, e.g., code that constitutes processor firmware, a protocol stack, a database management system, an operating system, or a combination of one or more of them.

A computer program, which may also be referred to or described as a program, software, a software application, an app, a module, a software module, a script, or code, can be written in any form of programming language, including compiled or interpreted languages, or declarative or procedural languages; and it can be deployed in any form, including as a stand alone program or as a module, component, subroutine, or other unit suitable for use in a computing environment. A program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub programs, or portions of code. A computer program can be deployed to be executed on one computer or on multiple computers that are located at one site or distributed across multiple sites and interconnected by a data communication network.

In this specification, the term "database" is used broadly to refer to any collection of data: the data does not need to be structured in any particular way, or structured at all, and it can be stored on storage devices in one or more locations. Thus, for example, the index database can include multiple collections of data, each of which may be organized and accessed differently.

Similarly, in this specification the term "engine" is used broadly to refer to a software-based system, subsystem, or process that is programmed to perform one or more specific functions. Generally, an engine will be implemented as one or more software modules or components, installed on one or more computers in one or more locations. In some cases, one or more computers will be dedicated to a particular engine; in other cases, multiple engines can be installed and running on the same computer or computers.

The processes and logic flows described in this specification can be performed by one or more programmable computers executing one or more computer programs to perform functions by operating on input data and generating output. The processes and logic flows can also be performed by special purpose logic circuitry, e.g., an FPGA or an ASIC, or by a combination of special purpose logic circuitry and one or more programmed computers.

Computers suitable for the execution of a computer program can be based on general or special purpose microprocessors or both, or any other kind of central processing unit. Generally, a central processing unit will receive instructions and data from a read only memory or a random access memory or both. The essential elements of a computer are a central processing unit for performing or executing instructions and one or more memory devices for storing instructions and data. The central processing unit and the memory can be supplemented by, or incorporated in, special purpose logic circuitry. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer readable media suitable for storing computer program instructions and data include all forms of non volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's device in response to requests received from the web browser. Also, a computer can interact with a user by sending text messages or other forms of message to a personal device, e.g., a smartphone that is running a messaging application, and receiving responsive messages from the user in return.

Embodiments of the subject matter described in this specification can be implemented in a computing system that includes a back end component, e.g., as a data server, or that includes a middleware component, e.g., an application server, or that includes a front end component, e.g., a client computer having a graphical user interface, a web browser, or an app through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network (LAN) and a wide area network (WAN), e.g., the Internet.

The computing system can include clients and servers. A client and server are generally remote from each other and typically interact through a communication network. The relationship of client and server arises by virtue of computer programs running on the respective computers and having a client-server relationship to each other. In some embodiments, a server transmits data, e.g., an HTML page, to a user device, e.g., for purposes of displaying data to and receiving user input from a user interacting with the device, which acts as a client. Data generated at the user device, e.g., a result of the user interaction, can be received at the server from the device.

While this specification contains many specific implementation details, these should not be construed as limitations on the scope of any invention or on the scope of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially be claimed as such, one or more features from a claimed combination can in some cases be excised from the combination, and the claimed combination may be directed to a subcombination or variation of a subcombination.

Similarly, while operations are depicted in the drawings and recited in the claims in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In some cases, multitasking and parallel processing may be advantageous.

What is claimed is:

1. A computer-implemented method for automatically updating a causal model, the method comprising:
   receiving, by a control system configured to automatically optimize a measure of quality of a batch of a biologic pharmaceutical, one or more external inputs;
   generating, by the control system and based on the one or more external inputs, one or more baseline values to a plurality of internal parameters, wherein the plurality of internal parameters define how the control system updates a causal model and how the control system determines which control settings to select given a current causal model;
   accessing, by the control system, a current causal model that measures one or more causal relationships between one or more control settings and the measure of quality of the batch of the biologic pharmaceutical;
   selecting, by the control system and based on the accessed current causal model and the plurality of internal parameters, one or more control settings that specify one or more controllable aspects of the batch of the biological pharmaceutical;
   repeatedly performing, using the control system, the following:
      selecting a configuration of input settings for manufacturing a batch of the biologic pharmaceutical based at least in part on the one or more control settings and the current causal model;
      automatically determining the measure of quality of the batch of the biological pharmaceutical manufactured based, at least in part one, the one or more control settings; and
      automatically adjusting, based on the measure of quality of the batch of the biological pharmaceutical, the current causal model.

2. The method of claim 1:
   the method further comprising adjusting the internal parameters based on the the adjusted causal model.

3. The method of claim 1, wherein the measure of quality of the batch comprises one or more of the following:
   a yield of the batch;
   a measure of an activity of the batch;
   a measure of an efficacy of the batch;
   a measure of impurities in the batch;
   a measure of a viability of transfected cells;
   a measure of transfection efficiency;
   a measure of a purity of the biologic pharmaceutical;
   a measure of monodispersion; or
   a measure of cell density.

4. The method of claim 3, wherein the purity of the biologic pharmaceutical comprises one or more of the following:
- a measure of host cell protein impurity;
- a measure of DNA impurity;
- a measure of RNA impurity; or
- a measure of host cell metabolite impurity.

5. The method of claim 1, wherein the control settings comprise one or more of the following:
- one or more settings related to processing steps;
- one or more settings related to a chemical composition of a substance;
- one or more settings related to physical control during manufacturing; or
- one or more settings related to purifying the batch of the biologic pharmaceutical.

6. The method of claim 5, wherein the settings related to processing steps comprise one or more of the following:
- an ordering of the processing steps;
- a time spent in each processing step;
- a time spent in each subprocess of a given processing step; or
- a choice of parameters for each processing step.

7. The method of claim 5, wherein the settings related to a chemical composition comprise a selection of one or more of:
- a nutrient media;
- an ion exchange resin;
- an affinity chromatography matrix;
- a polymer;
- a wash buffer; or
- an elution buffer.

8. The method of claim 5, wherein the settings related to physical control during manufacturing comprise one or more of:
- a time of manufacturing;
- a time of purification;
- a temperature during manufacturing;
- a temperature during purification;
- a humidity during manufacturing;
- a humidity during purification;
- a flow rate used during manufacturing;
- a flow rate used during purification;
- a g-force used during manufacturing;
- a measure of magnetism used during manufacturing;
- a measure of electricity used during manufacturing; or
- a measure of agitation used during manufacturing.

9. The method of claim 5, wherein the settings related to purifying the batch of the biologic pharmaceutical comprise purifying the batch using one or more of:
- electrostatic interactions;
- hydrophobic interactions;
- hydrophilic interactions;
- affinity chromatography; or
- size exclusion chromatography.

10. The method of claim 1, wherein:
- selecting the configuration further comprises selecting the configuration based on the causal model and a predetermined set of external variables; and
- the method further comprises adjusting control parameters that parameterize the impact of the predetermined set of external variables.

11. The method of claim 10, wherein the predetermined set of external variables comprises one or more external variables related to an environmental climate during manufacturing.

12. The method of claim 11, wherein the external variables related to the environmental climate comprise one or more of the following:
- a humidity during manufacturing;
- an external temperature during manufacturing; or
- a level of light during manufacturing.

13. A system comprising one or more computers and one or more storage devices storing instructions that when executed by the one or more computers cause the one or more computers to perform the operations of the method of claim 1.

14. One or more non-transitory computer-readable storage media storing instructions that when executed by one or more computers cause the one or more computers to perform the operations of the method of claim 1.

15. The method of claim 1, wherein the plurality of internal parameters comprises at least one of one or more spatial extents and one or more temporal extents.

16. The method of claim 1, wherein the external inputs define a search space of possible combinations of control settings.

17. The method of claim 1, wherein the internal parameters include one or more clustering parameters that define the hyperparameters of the clustering technique that is used by the control system.

* * * * *